US005487873A

United States Patent [19]
Bridges et al.

[11] Patent Number: 5,487,873
[45] Date of Patent: Jan. 30, 1996

[54] METHOD AND APPARATUS FOR TREATING HAZARDOUS WASTE OR OTHER HYDROCARBONACEOUS MATERIAL

[75] Inventors: Jack E. Bridges; Guggliam C. Sresty, both of Chicago; Allen Taflove, Wilmette, all of Ill.

[73] Assignee: IIT Research Institute, Chicago, Ill.

[21] Appl. No.: 335,190

[22] Filed: Nov. 7, 1994

Related U.S. Application Data

[63] Continuation of Ser. No. 190,737, Feb. 2, 1994, abandoned, which is a continuation of Ser. No. 66,624, May 24, 1993, abandoned, which is a continuation of Ser. No. 938,304, Aug. 28, 1992, abandoned, which is a continuation of Ser. No. 502,322, Mar. 30, 1990, abandoned.

[51] Int. Cl.$^6$ ........................................................ B09B 3/00
[52] U.S. Cl. ........................... 588/212; 422/305; 422/307; 219/679; 373/47; 373/147
[58] Field of Search ............................. 422/22, 184, 244, 422/251; 219/10.41; 373/39, 47, 147

[56] References Cited

U.S. PATENT DOCUMENTS

| Re. 30,738 | 9/1981 | Bridges et al. |
|---|---|---|
| 2,114,345 | 4/1938 | Hayford . |
| 2,459,622 | 1/1949 | Cohoe et al. ............... 219/10.41 |
| 2,486,684 | 11/1949 | Schlesman et al. . |
| 2,542,028 | 2/1951 | Hodge . |
| 2,731,208 | 1/1956 | Dodd . |
| 3,095,359 | 6/1963 | Heller . |
| 3,215,539 | 11/1962 | Landy . |
| 3,261,140 | 7/1966 | Long et al. . |
| 3,494,723 | 2/1970 | Gray . |
| 3,494,724 | 2/1970 | Gray . |
| 3,547,577 | 12/1970 | Lovercheck . |
| 3,753,651 | 8/1973 | Boucher . |
| 3,885,915 | 5/1975 | Utsumi et al. . |
| 3,926,556 | 12/1975 | Boucher . |
| 3,948,601 | 4/1976 | Fraser et al. . |

(List continued on next page.)

FOREIGN PATENT DOCUMENTS

| 1123705 | 11/1984 | U.S.S.R. . |
|---|---|---|
| 1406789 | 9/1975 | United Kingdom . |

OTHER PUBLICATIONS

Serota, R., "Heating with Radio Waves", Automation (Sep. 1973). pp. 2–6 only.

Bridges, J. E., et al., "RF/Microwave Volume–Reduction And Stabilization Systems For Radwaste Resins," presented at the Waste Management 1986 Symposium on Radioactive Waste Management.

"Dielectric Heating: RF and Microwave", EPRI Center for Materials Fabrication, Tech. Commentary, vol. 4, No. 1 (1987) pp. 1–4 only.

Lindroth, D., "Microwave Drying of Fine Coal", Technology news, Bureau of Mines, United States Department of the Interior, No. 282 (Aug. 1987).

Paul, B., "Combustion Says Firm Sterilizes Medical Waste with Microwaves", Wall Street Journal, Apr. 10, 1989, p. B3.

"A Microwave Sterilizer is Developed", New York Times, Science Watch, Jun. 20, 1989.

Hall, Steven K., "Infectious Waste Management: A Multi-faceted Problem," Pollution Engineering, 74–78 (Aug. 1989).

"Medical Waste Treatment by Microwave Technology", product brochure, Norcal Solid Waste Systems, publication date unknown.

"Dielecttric Heating", product brochure, PSC, Inc., publication date unknown.

*Primary Examiner*—Lyle A. Alexander
*Attorney, Agent, or Firm*—Fitch, Even, Tabin & Flannery

[57] ABSTRACT

Methods and apparatus for treating waste with radio frequency include a wall defining a radio frequency treatment chamber through which waste may be passed. A source of radio frequency energy energizes the radio frequency treatment chamber to heat the waste and drive off vapors therefrom leaving solid residue to be disposed of. A guard heater and/or insulation maintains the wall at substantially the same temperature as the waste being heated by the radio frequency to prevent vapors from condensing on the waste.

10 Claims, 19 Drawing Sheets

U.S. PATENT DOCUMENTS

| | | |
|---|---|---|
| 4,140,180 | 2/1979 | Bridges et al. . |
| 4,144,935 | 3/1979 | Bridges et al. . |
| 4,148,614 | 4/1979 | Kirkbride . |
| 4,175,885 | 11/1979 | Jeppson . |
| 4,250,139 | 2/1981 | Luck et al. . |
| 4,252,459 | 2/1981 | Jeppson . |
| 4,252,487 | 2/1981 | Jeppson . |
| 4,276,093 | 6/1981 | Pickerman . |
| 4,347,016 | 8/1982 | Sindelar et al. . |
| 4,376,033 | 3/1983 | Calderon . |
| 4,376,034 | 3/1983 | Wall . |
| 4,398,076 | 8/1983 | Hanson . |
| 4,449,585 | 5/1984 | Bridges et al. . |
| 4,457,221 | 7/1984 | Geren . |
| 4,476,926 | 10/1984 | Bridges et al. . |
| 4,485,868 | 12/1984 | Sresty et al. . |
| 4,485,869 | 12/1984 | Sresty et al. . |
| 4,498,535 | 2/1985 | Bridges . |
| 4,524,079 | 6/1985 | Hofmann . |
| 4,524,827 | 6/1985 | Bridges et al. . |
| 4,545,435 | 10/1985 | Bridges et al. . |
| 4,619,550 | 10/1986 | Jeppson . |
| 4,645,004 | 2/1987 | Bridges et al. . |
| 4,670,634 | 6/1987 | Bridges et al. . |
| 4,710,318 | 12/1987 | Horiuchi et al. . |
| 4,746,968 | 5/1988 | Wear et al. . |
| 4,775,770 | 10/1988 | Fritz . |
| 4,801,427 | 1/1989 | Jacob . |
| 4,808,782 | 2/1989 | Nakagawa et al. . |
| 4,808,783 | 2/1989 | Stenström . |
| 4,818,488 | 4/1989 | Jacob . |
| 4,917,586 | 4/1990 | Jacob . |
| 4,931,261 | 6/1990 | Jacob . |
| 4,943,417 | 7/1990 | Jacob ........................ 422/22 |
| 4,978,501 | 12/1990 | Diprose et al. ............ 422/22 |
| 5,076,727 | 12/1991 | Johnson et al. . |

(a) $TE_{10}$ MODE POWER DENSITY (b) $TE_{20}$ MODE POWER DENSITY (c) $0.864\ TE_{10} + 0.48\ TE_{20}$ POWER DENSITY

FOR $X_1 \ll R_1$ $$W = \frac{V^2}{R} = V^2 \sigma$$

FOR $X \gg R_1$ $$W = I_N^2 R_N = \left(\frac{V}{X}\right)^2 R$$

$$= \left(\frac{V}{X}\right)^2 \frac{1}{\sigma}$$

METHOD AND APPARATUS FOR TREATING HAZARDOUS WASTE OR OTHER HYDROCARBONACEOUS MATERIAL

This application is a continuation of application Ser. No. 190,737 filed Feb. 2, 1994 now abandoned, which is a continuation of application Ser. No. 066,624 filed May 24, 1993 abandoned, which is a continuation of application Ser. No. 07/938,304 filed Aug. 28, 1992, abandoned, which application is a continuation of application Ser. No. 502,322 filed Mar. 30, 1990 now abandoned.

BACKGROUND OF THE INVENTION

This invention relates to a method and apparatus for treating hazardous wastes or other hydrocarbon-bearing materials, such as municipal wastes or coal, so that the final product is rendered innocuous or made more valuable. Hazardous wastes suitable for processing using this invention include soils and earth contaminated with fuels, solvents, etc.; sludges produced from various chemical and petrochemical processes such as desalting sludges and still bottoms; filter cakes containing organics such as those produced in the ink and dry cleaning industries; and waste solvents. Alternatively, where appropriate, valuable products can be recovered wherein the residues are easily disposable and the effluents are readily treated. In particular, the invention relates to a method and apparatus for using radio frequency energy to heat waste materials, drive off effluents including water, volatilize hydrocarbons and the like, and inactivate microorganisms and possibly pyrolyze dried hazardous waste in order to produce a harmless residue of reduced volume for disposal and an easily treatable effluent. Radio frequency heating reduces the solids volume so that relatively little space is needed for long term and safe storage of the reduced volume residue. In many cases the results of the heating generate effluents and residues which are either commercially valuable or easily treated.

Some of the conventional processes for treating hazardous waste, such as incineration or thermal treatment using steam or hot gases, produce additional waste gases which must be disposed of properly. Alternative methods such as solidification of the waste followed by disposal in landfills, are expensive and occupy considerable quantities of space in the landfill. Additionally, disposal of solidified waste in landfills may result in long-term migration of the hazardous components into groundwater sources due to deterioration of the landfill liner.

It is known that heating waste materials drives off water and reduces the volume of the waste. There have been various proposals to use various heat sources first to dehydrate the wastes and then subsequently further treat the wastes to render hazardous materials innocuous or to recover valuable products. Such heating methods include the use of electrical heaters, combustors, incinerators, and fluidized bed heat transfer methods. These techniques generally lead to the production of considerable amounts of waste gases. In many cases such waste gases may contain organic toxic compounds or radioactive components, and these are often vented into the atmosphere. As such, they may pose significant environmental and health hazards. Other types of heating methods such as the use of heater kilns, generally result in over and underheating. This lack of temperature control generates new species of products of unknown health hazards. Such new products pose major difficulties in obtaining permits for such processes. Such nonuniform heating processes are also subject to mechanical failure due to sticking or the development of scale or char in the apparatus.

It has been proposed that it may be easier to heat wastes such as radioactive contaminated ion-exchange resins uniformly by exposing them to microwave power, rather than by using conventional heat sources; however, using microwaves to treat resin presents a number of other problems. If a mass of resin is heated by microwaves using conventional apparatus, heat loss from the resin mass at its surfaces due to conduction, convection or radiation results in temperature variations throughout the resin, which is highly undesirable. In Bridges, J. E. et al., "RF/Microwave Volume-Reduction and Stabilization System For Radwaste Resins," presented at the Waste Management 1986 Symposium on Radioactive Waste Management, it was disclosed that radio frequency energy and microwave energy produced by an RF power source and fed to an RF reactor, which could be sealed with radioactively contaminated ion exchange resin inside, may be used for the volume reduction and stabilization of those resins. In particular, it was there suggested that radioactive ion exchange resin beads can be treated by exposing them to microwave radiation, which drives off water left over from ion exchange processes. Effluents from the RF reactor are fed to a vapor/liquid separator; gases from the vapor/liquid separator are received by a causticized carbon absorber; and liquids are pumped from the bottom of the separator to an activated carbon absorber.

Other methods of heating materials are known for use in different environments. For instance, see Bridges et al., U.S. Reissue Pat. No. Re. 30,738 for Apparatus and Method for In Situ Heat Processing of Hydrocarbonaceous Formations, which discloses a method and an apparatus for heating buried materials, such as oil shale, bitumen, and the like. The apparatus employs a central exciter plate or equivalent electrode and a pair of grounded plates or equivalent electrodes outside it. The electrodes receive radio frequency energy and produce a transversely uniform radio frequency electric field for heating, by displacement current, the buried material bounded by the electrodes. In order to provide even more uniform heating of the buried deposits by such an apparatus, a method of and apparatus may be used for repetitively switching or altering the electrical termination of the electrodes of the apparatus to vary the longitudinal standing wave patterns of the electric field, as disclosed in U.S. Pat. No. 4,449,585 to Bridges et al. for Apparatus and Method for In Situ Controlled Heat Processing of Hydrocarbonaceous Formations.

Considerable prior art exists relative to drying paper and wood products, sand cores for casting, drying foods, as well as setting resins in plywood, vulcanization of rubber, cooking bacon, sulfur removal from coal, or as a replacement for evaporators or thin-film dryers. In general, such applications have emphasized the use of microwave energy except in the case of drying processes for textiles, paper, wood products and the setting of molds. Such applications have not required careful control of the emitted vapors and generally rely on the vaporization of water to terminate the heating process.

Typical of microwave processes are those described in "Microwave Drying of Coal" published by David Lindroff of the Twin Cities Research Center, Bureau of Mines, Minneapolis, Minn. Comparable arrangements have been proposed by Jeppson U.S. Pat. Nos. 4,619,005 and 4,252,487 as well as Sindelar U.S. Pat. No. 4,347,016 and by Pickerman U.S. Pat. No. 4,256,093. The latter patents address the problem of heating asphalt fragments by microwave energy for recycling of asphalt paving.

Kirkbride U.S. Pat. No. 4,148,614 proposed an arrangement similar to that described by Lindroff wherein coal is exposed to microwave radiation with the objective of reducing the sulfur content. Such microwave systems appear to be impractical for large scale processing owing to the reduced depth of penetration of the microwave energy into the coal along with problems of refluxing and vapor control associated with the high temperatures needed to desulfurize the coal.

In all such above cases, no control of the vapors or effluents is taught. No features are offered to prevent heat loss to the walls of the radio frequency or microwave heating unit.

Others such as Hanson U.S. Pat. No. 4,389,076 proposed heating hydrocarbonaceous material such as oil shale by passing the oil shale through a ceramic tube which penetrates cleanly through a microwave oven or cavity. Other complex systems have been proposed by Hodge U.S. Pat. No. 2,542,028, Schlesman U.S. Pat. No. 2,486,684, and Wall U.S. Pat. No. 4,376,034. All such arrangements suffer from the aforementioned difficulties; however, Wall discloses a feature which uses a preheating step whereby the vapors derived from the hot shale are allowed to condense on the cooler incoming shale as a technique to preheat the oil shale and to conserve energy. Such a process leads to the generation of unwanted species since the same molecule is progressively reheated several times which can result in products with very high pour points or with highly toxic or carcinogenic properties. Wall also proposes to use an airtight chamber with suitable air-locks on the incoming and output ports; however, he does not describe a system where the vapors are progressively drawn off from different temperature regions of the material, nor does he describe a lower frequency system which is more suitable for processing large volumes of material, nor does he describe the need for fluid uniformity or other means to obtain uniform temperatures.

Calderon U.S. Pat. No. 4,376,033 discloses heating oil shale by thermal conduction from the hot walls. In this instance, no high frequency or microwave heating process is employed. Calderon proposes to use electrical induction heating to heat the walls.

Wear U.S. Pat. No. 4,746,968 discloses a combination microwave drying cavity and an infrared thermal radiator that complements the microwave radiation to effect a more uniform drying of a product within the cavity. In the case of Wear, the material when heated above 100° C. apparently lost nearly all of its ability to absorb microwave energy. As a consequence, the infrared heaters were used to provide additional heating. Thus, in Wear's case, energy is transferred from a heated plate by irradiation to the material. If the surface is too hot, the material becomes sticky and gummy and thereby eventually clogs the mechanics of the system. On the other hand, if the wall material is significantly lower than that of the material being processed, energy is lost from the material being processed. In the case of wet or moist material where a high energy absorption occurs, this may not be a significant problem but it can be significant in the case of very dry materials. These have little absorbing ability and therefore have little capability to simultaneously heat themselves and the adjacent walls.

SUMMARY OF THE INVENTION

The use of RF heating has a number of basic intrinsic advantages over conventional thermal treatment methods. Specifically, the processing atmosphere can be totally controlled. As a result, any valuable products which are produced are not diluted by combustion gases and therefore are easily recovered. Also, better control of chemical reactions can be made. A special advantage of the RF treatment method is that gaseous effluents can be held to 1/1000 of that associated with incineration. The noxious compounds are not diluted and are more easily treated or recovered. Bag houses, precipitators and scrubbers are not needed. In the case of residue treatment, small particulates and heavy metals are retained in the residue. Many residues can be treated so that they are encapsulable in cement. In other instances the residues are marketable. By proper design of the RF applicator, uniform and/or controlled heating is possible such that excessive temperatures are not created, and this suppresses the generation of a new species of unknown health hazard characteristics. Also, by uniform and controlled heating, the sticking and particle size restrictions can be eased and large volumes of material can be heated without the requirement for size reduction of the waste materials. The process is also thermally and economically efficient because higher value products can be recovered and the combustion can be efficiently conducted at the electric power generation plant.

Other hydrocarbon materials such as upgraded municipal wastes are often used in waste-to-energy projects. This requires the combustion of the waste to generate steam which, in turn, is used to power an adjacent electrical power plant. One of the problems with this approach is the permitting of the facility itself since the stack gases might contain not only the usual combustion products but noxious products contained in the wastes. Thus, a fairly expensive and elaborate stack gas clean-up system will be required. In addition to the steam boiler, an electric power plant is also required. This results in high capital equipment along with the attendant problems to make the process environmentally acceptable. As an alternative to a no-emissions processing of waste, the hydrocarbon-rich bearing materials could be pyrolyzed by radio frequency heating in a closed container. Vapors generated by the pyrolysis contain valuable products such as oils and acetic acids. In addition, the input waste volume is significantly reduced to a black friable carbon char. With further treatment this could be used as an alternative to carbon black which is used in a variety of applications, principally in the manufacture of rubber tires. The alternative RF process also offers the possibility of reduced capital costs since the fairly simple reactor coupled with the RF power source is required, thereby eliminating the boiler, the stack gas clean-up and the electrical power generation plant of the conventional waste-to-energy facility.

A similar problem exists due to the high sulfur content of most coals. It is known that the treatment of coal by radio frequency energy coupled with heat tends to desulfurize the coal. In addition, partial pyrolysis can also drive off valuable liquids which have a higher market value than the coal itself. Thus, an RF partial pyrolysis unit which treats large volumes of coal offers the possibility of sulfur reduction, recovery of high market value liquids while at the same time offering a residue which can be combusted in a standard coal fired power plant. Alternatively, the coal could be fully pyrolyzed and the resultant high carbon char used in the gasification process, the gas from which would fuel gas turbines to generate electrical power. Such a process offers the opportunity to clean up the sulfur components in an undiluted form prior to combustion. Thus, the RF processing of coal, in a closed container without emissions, offers the possibility for further reductions and harmful emissions into the environment.

This invention, since it addresses the problem of heating large quantities of waste material through the vaporization point of water and to much higher temperatures, solves several severe technical problems. Typically, when the water is evaporated from the material under treatment, it loses much of its ability to absorb energy via dielectric heating. Thus, much higher field intensities are employed and, in so doing, means are included to prevent arcing. Excessive increases of temperature in local areas should be suppressed. There is thus provided a uniform temperature rise in the context of reasonably uniform or time-averaged electric fields. A uniform electric field is where the average heating effects of a combination of unperturbed electric fields (fields in the reactor without waste material) are reasonably uniform, either by the intrinsic nature of the applicator or by combination of complimentary modes. Also, the electric field penetration into the material itself is made reasonably uniform. As a consequence, the depth of penetration is a major consideration and, in the case of large volumes of material, lower frequencies below the microwave region are used since, the higher the frequency, the smaller the depth of penetration. Alternatively, if the unperturbed electric field is nonuniform, the nonuniformities can be averaged out by moving the material with respect to the standing wave patterns of the field or by tumbling the materials.

An apparatus and method for treating hazardous waste with radio frequency energy in the form of a radio frequency electric field, according to the present invention, enjoys a number of advantages over the prior apparatus and methods. One advantage of the instant apparatus is that it is able to heat uniformly a continuous stream or semi-continuous flow of hazardous waste without introducing any additional fluids such as steam or combustion products into the hazardous waste. This permits recovery of the effluents containing the volatiles, solvents, steam, fuels, and the like that are released from heating of the hazardous waste in a concentrated form. The contaminants can be economically recovered, and either disposed of safely or recycled.

Another advantage of the present invention is that it allows a stream of hazardous waste to be pyrolyzed within a limited temperature range to prevent the formation of unwanted compounds during processing. A further advantage of the instant invention is that it provides a continuous or semi-continuous type RF heating retort or reactor which provides easily controlled heating despite changes in electrical properties as the the stream of waste being treated is traversed longitudinally. A still further advantage of the instant invention is that it uniformly heats hazardous waste without risking arcing and unwanted overheating or underheating of the hazardous waste, thus eliminating problems with electrical breakdown near the hazardous waste. Finally, the apparatus prevents the release of hazardous substances, in particular, organic effluents to the environment.

The present invention provides improvements in methods of and apparatus for treating a stream of hazardous waste to provide controlled heating of the hazardous waste.

Heating is provided by having the hazardous waste in a stream flow through a treatment volume of the reactor. Radio frequency energy is then supplied to the reactor causing a time-varying or alternating electric field to be created in the treatment volume thereof. In order to heat the hazardous waste even more uniformly, a plurality of electrical resistance guard heaters surround the treatment volume of the reactor so that a large temperature gradient is not present at the periphery of the treatment volume. The use of guard heaters along the walls of the heating chamber makes the wall temperature approximately the same temperature as that of the material being processed. Alternatively, insulated wall materials which have low thermal conductivity and heat capacity may be used such that as the wall is heated, the wall temperature can immediately rise to the temperature of the material being processed.

Without the guard heaters and/or insulation, the loss of heat to the outermost portions of the reactor results in preferential cooling of the outer portions of the hazardous waste being treated and may lead to condensation of previously vaporized organic effluents which may react; in particular, they may polymerize on the cooler outer portions of the partially treated hazardous waste.

The technical features of this invention include the case where heating consists of both de-moisturizing the material and heating very low loss material well above the vaporization point. Alternatively, it may simply be to heat predried material or low moisture material to relatively high temperatures. Such temperatures would range from 100° C. for drying purposes to temperatures where significant distillation or pyrolysis may also occur. The process could be considered as either a batch or continuous process.

In the case where large volumes of material are to be processed, the use of microwave energy is inappropriate because of depth of penetration limitations. As a consequence, lower frequencies are used at higher field intensities with a resultant requirement of field uniformity to prevent arc-overs, corona discharges or other deleterious effects associated with high voltages. In addition, control of the field intensity where partial pyrolysis or pyrolysis is occurring is also used to prevent the generation of new species on hot spots and to prevent thermal runaway. This happens if the temperature is increased to about 300° C. and the ability of the material to absorb energy increases dramatically with temperature.

The processes described here involve the minimization or total elimination of the refluxing of moisture and other condensable vapor constituents. The refluxing problem is overcome in a batch or semi-continuous process wherein the temperature of all materials are rising together during heating and the vapors are drawn from the nearly constant temperature materials in a progressive fashion. This does require the wall temperatures of the oven to track the temperatures of the material being heated, and that the material being heated is sufficiently permeable that the effluent gases can be promptly withdrawn.

In the case of a continuous process, little or no refluxing can be tolerated. Otherwise, as the cool moist material enters the heating chamber, the vapors from the heated material would condense on the incoming material. This would cause nonuniform distribution of conductivities and could lead to hot spots and resulting arc-over because of electric field enhancements. This refluxing process would continue until the incoming materials were saturated with water or until considerable condensation occurred on the walls of the chamber. The wall temperature should exceed the vaporization temperature of the water or any other major constituents. In addition, again in the case of a continuous process, vapors from lower temperature materials are not mixed with those from other temperature levels, especially vapors which are the by-products of pyrolysis. If the products of high temperature distillations are allowed to condense on materials with lower temperatures, the generation of new species, polymerization and other undesirable effects might occur. If the products of distillation from low temperature products are allowed to be commingled with those from the high temperature steps of the process, the possibility of a recombination of these volatiles into new species on catalytic centers of the material being processed must also be considered along with the added difficulty of separation of products otherwise separable by a more orderly distillation process. Again, the temperatures of the wall must track the temperatures of those products being processed.

The present invention gives consideration to heat losses of material being processed due to black body radiation and gaseous convection. For example, in the case of coal on a conveyor belt, passing through drying systems, if higher temperatures are needed above that required for drying, the surface of the coal will exchange energy via black body radiation with the inner surfaces of the reactor. This causes a pronounced cooling effect, particularly if the coal is near the surface. In addition, gaseous convection and heat-pipe condensation on the reactor walls will take place. This further cools the coal and thereby requires increasing the electric field intensity to provide the required temperature increase. Such an increase leads to electrical breakdowns, arcing and sparking between coal particles, and other difficulties leading to inefficient and impractical operation.

The present invention also takes into account the differences in the ability of materials being heated to absorb electrical energy when initially introduced as moist material into the reactor as compared to when it has been nearly dehydrated. For example, it takes three to ten times more energy to simply dry a relatively moist material at temperatures up to 110° C. than to heat the material from 110° to 300° or 400° C. While the reduction in heating requirements above 110° C. may well offset the loss and ability to absorb electromagnetic energy when the material is dried, the design of any continuous reactor must take into account these varying energy requirements. The design must either grade or shape the fields in a way such that, while the flow rate is continuous, the energy deposition rate is such that adequate dehydration is achieved while at the same time further heating is accomplished as the material flows through the reactor. A possible design change to alleviate coordination of the heating would be to use two reactors, one, in essence to dry the materials, and the other to further process the material above 110° C. Above 110° C., a reactor employing a higher frequency source may be desirable. The reason for this is that the dielectric properties after the moisture has been removed remain reasonably constant and, therefore, permit the design of a more tractable and simple reactor.

The present invention also takes into account the difficulty in the apparatus shown in Lindroff wherein the electric fields produced by the microwave horns in the retort eventually occupy nearly the entire volume of the retort despite the "garden hose spray" configuration employed. This occurs because of the dielectric mismatch between the coal and the microwave energy as the microwave energy impinges upon the coal. As a consequence, a significant portion of the energy is rescattered at the surface of the coal back into the entire retort itself. Thus, the microwave energy interacts with the entire volume of the retort causing current flow around the entire walls and thereby decreasing the efficiency. Also, Lindroff, as shown, does not assume proper control by withdrawing moist air from the center of the dryer.

More importantly, the coal particles or other particles have a propensity to depolarize the electric field. For example, if a spherical or cylindrical dielectric particle is exposed to a free electric field, the internal field is less by a significant fraction than the free field. For spheres and infinite cylinders, the internal fields $E_i$ are given in terms of the unperturbed field $E_o$ as in the following equations:

$$\text{Sphere: } E_i = \frac{3}{E_R + 2} E_o \quad (1)$$

$$\text{Cylinder: } E_i = \frac{3}{E_R + 1} E_o \quad (2)$$

where $E_R$ is the relative dielectric constant.

Typical values of $E_R$ range from 100 for moist materials to 5 for dry material. The reduced internal fields are only 3 to 30% of a typical free field. In the case of waste material between nearly parallel plate electrodes, any air gap between the material and electrodes reduces the internal voltage. Small air gaps are tolerable and have the advantage of suppressing runaway heat effects. However, excessively large air gaps in effect reduce the heating rates for a given field and require increasing the field intensity with commensurate problems of air breakdown, arc-overs and carbon surface formations. Thus, the space between the electrodes should be at least 50 to 90% filled if possible, while at the same time, the particles are experiencing a suitable tumbling or mixing operation.

In the case of microwave heating such as illustrated by Lindroff, the depolarization effect is better characterized as a wave-impedance mismatch at the interface between the air and the coal. This mismatch causes the energy to be largely rescattered in the treating unit.

It is thus a principal aspect of the present invention to provide an apparatus and method for heating hazardous waste with radio frequency energy to drive off hazardous effluents.

It is another aspect of the present invention to provide a means and apparatus for heating hazardous waste to an elevated temperature using radio frequency energy followed by removing the contaminants from the hazardous waste with the help of a sweep gas.

It is another aspect of the present invention to provide an apparatus and method for heating hazardous waste without venting contaminated gases to the environment.

It is another aspect of this invention to inject steam to strip the hydrocarbons from the materials being processed.

These and other aspects and advantages of the present invention will become apparent from the following detailed description, particularly when taken in conjunction with the accompanying drawings.

DETAILED DESCRIPTION OF THE PREFERRED EMBODIMENTS

Figure 1:
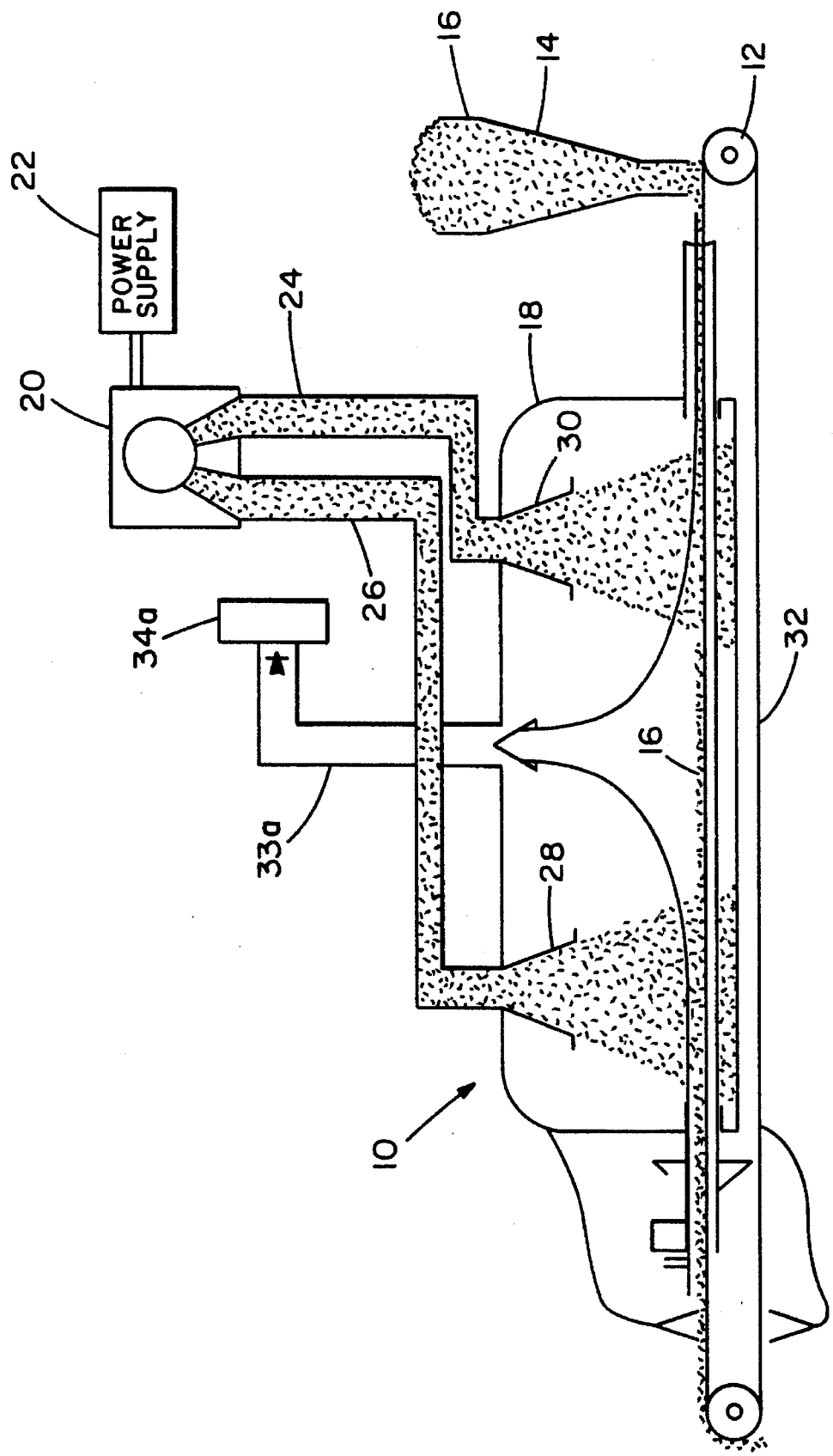
FIG. 1 is a schematic diagram of a prior art microwave system showing details of a microwave generator, wave guides, horns and a conveyor for carrying coal to be dried.

FIG. 1 shows a microwave drying system 10 of the prior art. The microwave drying system includes a conveyor 12 adapted to carry a quantity of coal 14 placed on the conveyor by a coal feeder 16. A microwave treatment chamber 18 has a microwave generator 20 and a power supply 22 for feeding microwave radiation through waveguides 24 and 26 to horns 28 and 30 within the treatment chamber 18. Coal 16 resting on the belt 32 of the conveyor 12 passes underneath the radiation from the waveguide horns 28 and 30. The radiation is propagated at substantially right angles with respect to the direction of motion of coal. Water is boiled from the coal along with other volatile compounds through a duct 33 which is connected to a blower 34. Note that the emitted vapor flows toward the cooler coal in some portions of the treatment chamber. Also, no effort is made to control the temperature of the chamber's walls. No effluent treatment system is disclosed.

Figure 2:
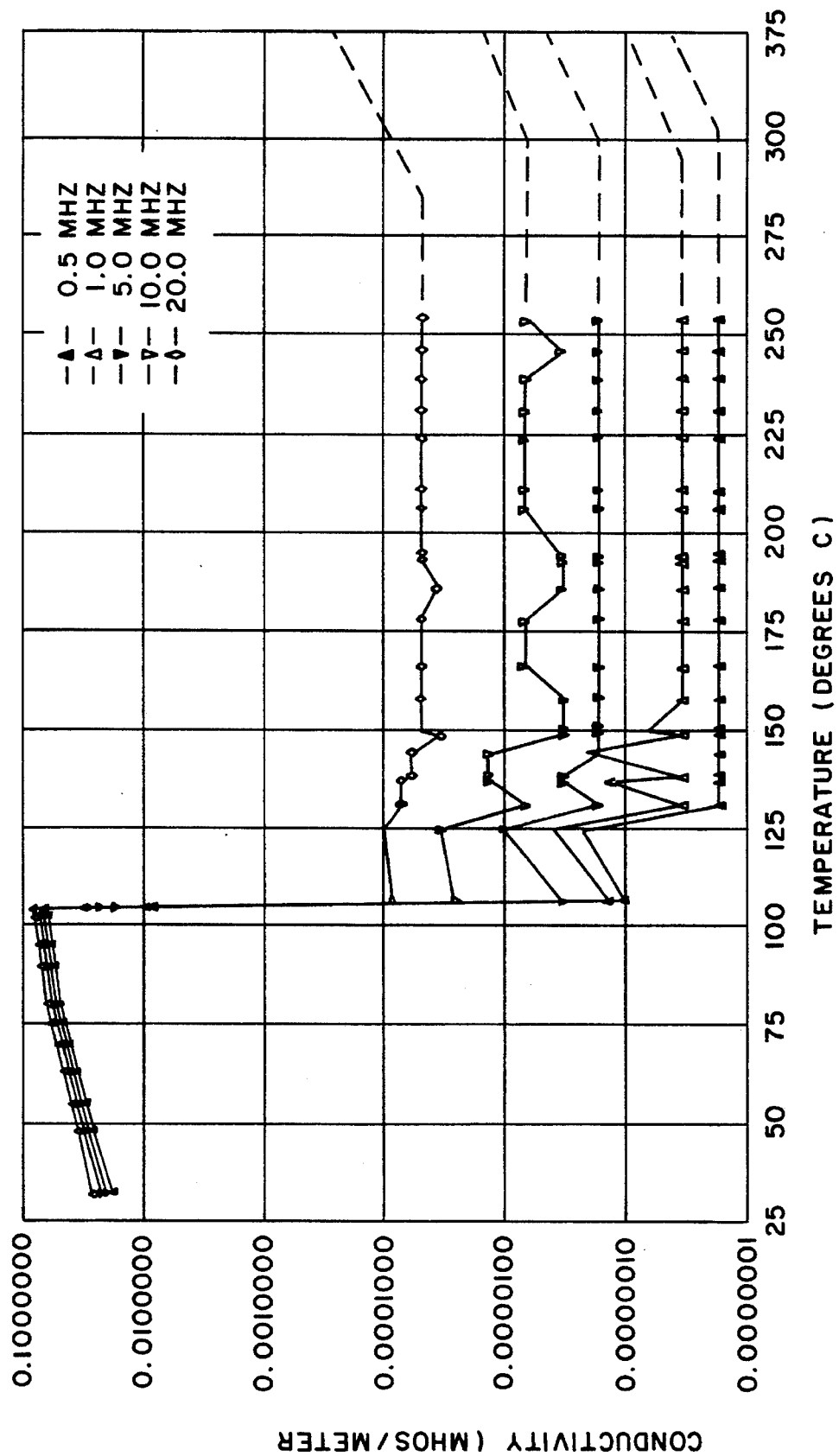
FIG. 2 is a graph of the temperature of a contaminated soil sample versus the conductivity of that sample at various frequencies of radio frequency current.

FIG. 2 illustrates the conductivity versus temperature of a sludge pond soil sample for selected frequencies. Since the heating rate is proportional to the square of the electric field times the conductivity, it is seen that materials which have a high moisture, usually at temperatures below 105° C., are relatively easy to heat for a given electric field. On the other hand, if the moisture is evaporated, it is seen that the conductivity changes at least three to five orders of magnitude, depending on the frequency. This means that the heating rate decreases significantly if the electric fields are held at the same level. To overcome this, electric field intensity must be increased or the frequency increased. In either case, neither the electric field intensity or the frequency can be increased beyond a certain point, severe equipment design problems and arcing can be expected. On the other hand, using an applicator such as described by Lindroff, increasing the frequency from the upper frequency at 20 MHz (as shown in FIG. 2) to the microwave band (with higher conductivity) is clearly not proportional to the frequency increase and may have no net practical benefit. The reason for this is that depolarization effects associated with the coal which, in effect, decrease the value of the electric field within the coal. Stated another way, the dielectric interface mismatch between the air and the coal results in considerable reflected energy. A portion of this reflected energy reenters the horn antenna and is absorbed in the circulator or isolator which is used in the microwave circuit. On the other hand, a more efficient method is to nearly fill the volume between two parallel plates (FIG. 4A or FIG. 4D) with the material. This results in a minimum depolarization and if some air gap occurs between the material and the exciter plates, suppression of runaway effects can also be realized.

Figure 3:
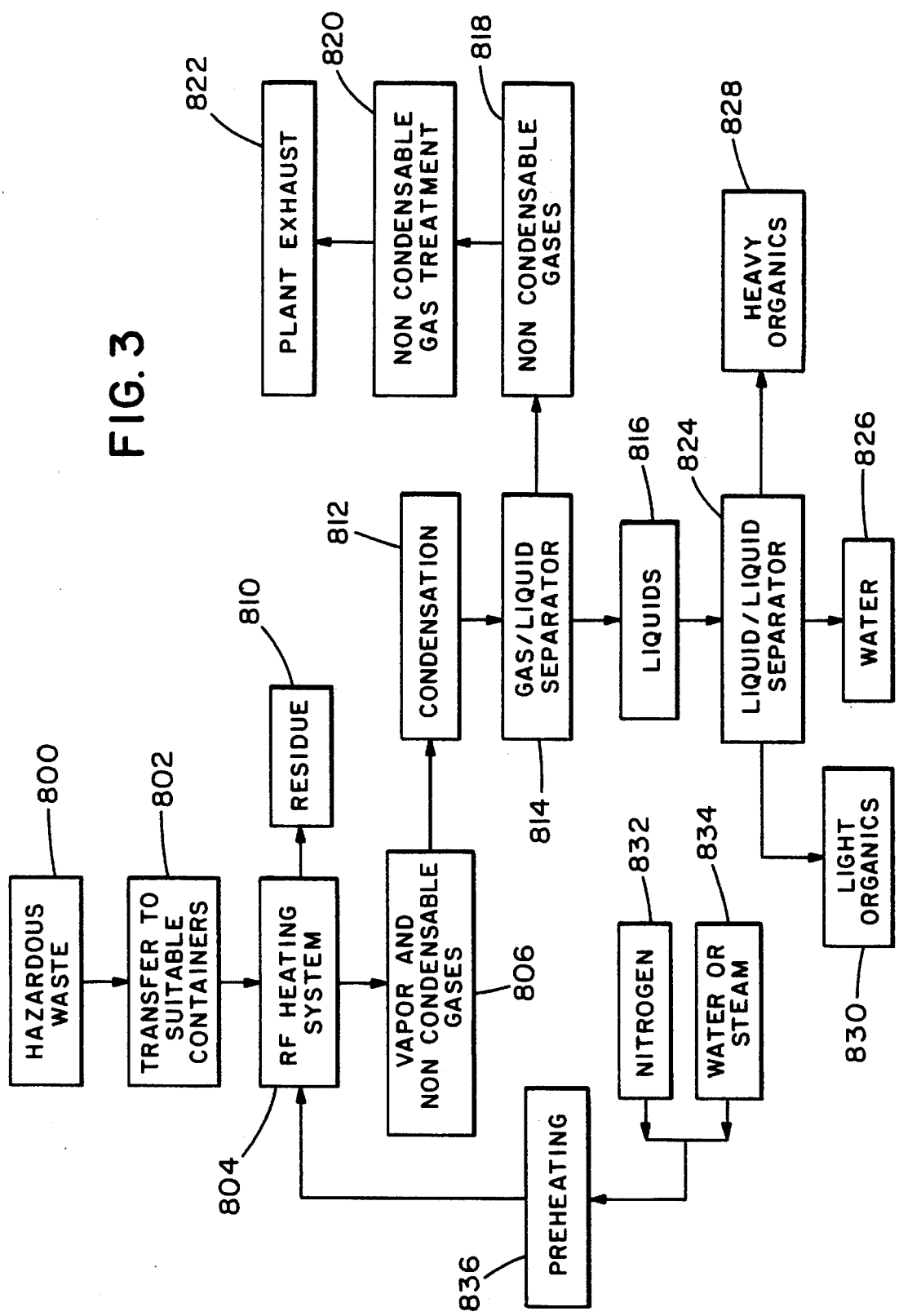
FIG. 3 is a flow chart detailing the steps in the method of treating hazardous waste embodying the instant invention.
Figure 18:
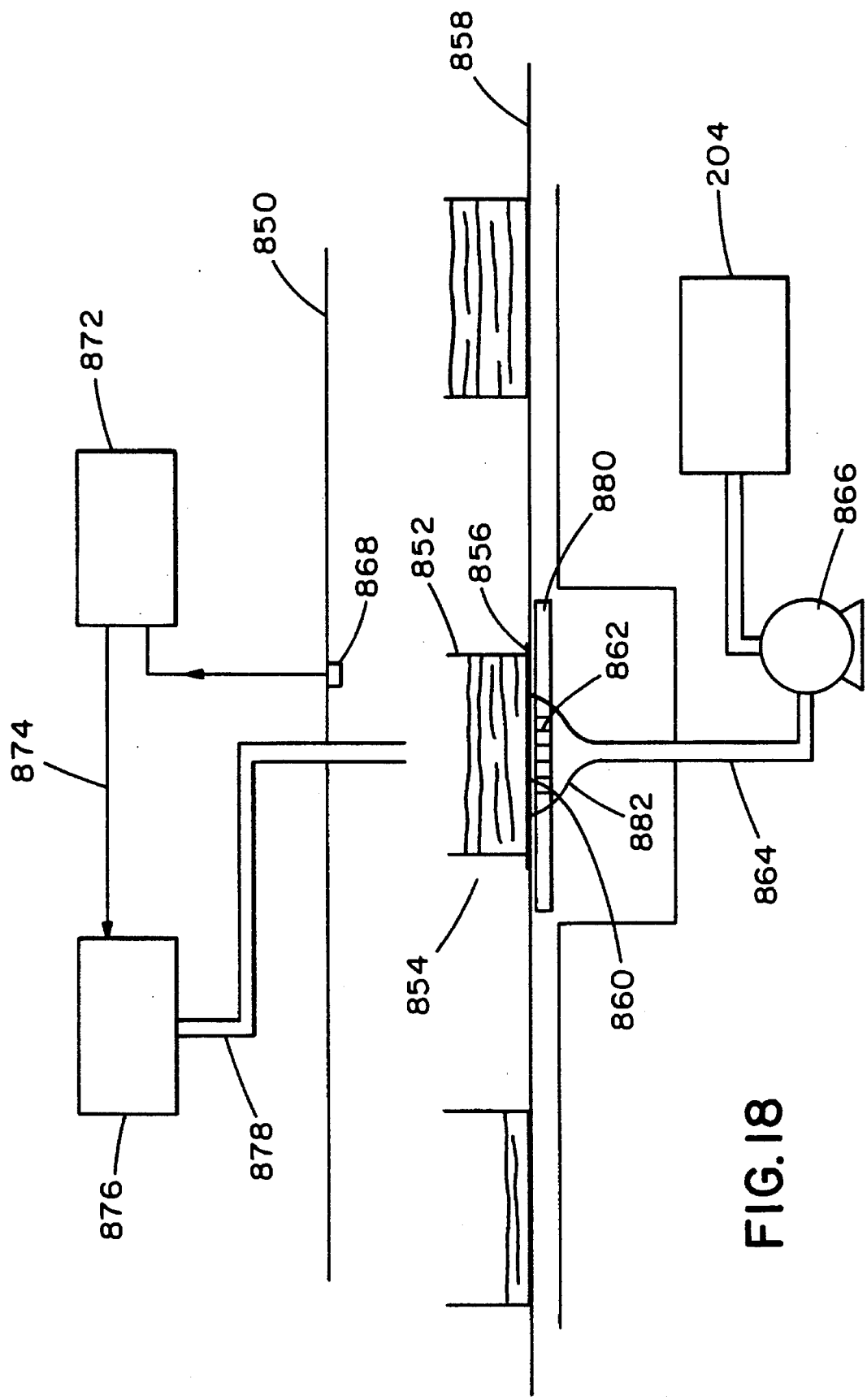
FIG. 18 is a view, partially diagrammatic, of a sweep gas injection and preheating system and an effluent treatment system useful with the systems shown in FIGS. 8 and 9.

FIG. 3 is a flow diagram that describes various steps that may be involved in the processing of hazardous waste using the current invention. In step 800, hazardous waste is received at the plant from a number of sources, including clients, and other locations within the plant. The hazardous waste may be received in steel barrels, plastic containers, or pumped as a liquid or slurry. The waste is transferred or pumped into suitable containers in step 802. It must be noted that the containers must be transparent to the applied radio frequency energy for use with certain embodiments of the invention such as the ones shown in FIGS. 8 and 9. The waste transfer step 802 can simply be a pumping system for use with certain other embodiments of the invention such as the ones shown in FIGS. 12 and 15. The hazardous waste is processed in the radio frequency heating chamber in step 804. Sweep gases that may include nitrogen introduced in step 832 or steam introduced in step 834 are injected into the hazardous waste while it is processed inside the radio frequency heating system to efficiently strip organics from the hazardous waste. The sweep gases may be preheated in step 836 to approximately the same temperature as the hazardous waste to prevent heat losses. It is also within the scope of the current invention to pump liquid water, and to generate steam during the preheating step 836. Energy required during preheating step 836 may be supplied by combustion of fuels or with electrical heaters. In certain instances, the hazardous waste may exhibit poor permeability to flow of fluids such as the above said sweep gases until it is heated to a certain temperature. An example of such an instance is hazardous waste containing soils and clays. The permeability of such materials can be as low as 1 millidarcy or lower. It is difficult to maintain a good flow of sweep gas through such waste. However, processing of the hazardous waste in the radio frequency heating system will render the waste permeable after reaching temperatures of about 100° C. through evaporation of certain moisture and organics, and the resulting porosity. The permeability of most hazardous waste materials increases by 1 to 3 orders of magnitude. It is within the scope of the present invention to initiate the flow of the above said sweep gases after the hazardous waste has reached a predetermined temperature as illustrated in FIG. 18. Still referring to FIG. 3, in step 810 the residue from processing of hazardous waste is removed from the radio frequency heating chambers for disposal. In step 806 vapors and non-condensable gases are removed from the radio frequency heating chamber using a suitable means such as a blower. The vapors are condensed to liquids in step 812. In step 814 the liquids are separated to step 816 from non-condensable gases to step 818 using suitable means such as demister pads. The liquids are further separated in step 824 using suitable gravity separation means into light organics to step 830 that have densities less than water, water to step 826, and heavy organics to step 828 that have densities greater than water. The non-condensable gases are treated in step 820 to remove the hazardous components using suitable means such as carbon adsorption 340, or to combust the hydrocarbons to produce carbon dioxide and water vapor using suitable means such as the catalytic oxidation system 95, and are vented to plant exhaust 822. Light organics in step 830 and heavy organics in step 828 may be further treated for disposal or recycling.

The radio frequency treatment unit includes an applicator or reactor 60 providing a reaction chamber to which radio frequency energy is applied. The design of the applicator 60 to produde the required electric field and exposure time is of interest. Such applicators may be divided into three basic groups: TEM parallel plate applicators, TE or TM controlled mode applicators, and multi-mode TE and TM applicators. Typically with the multi-mode TE or TM applicators, the modes are not controlled such that a number of peaks and nulls of the electric field exist within the heating unit, such as exists typically in a microwave oven.

Figure 4A:
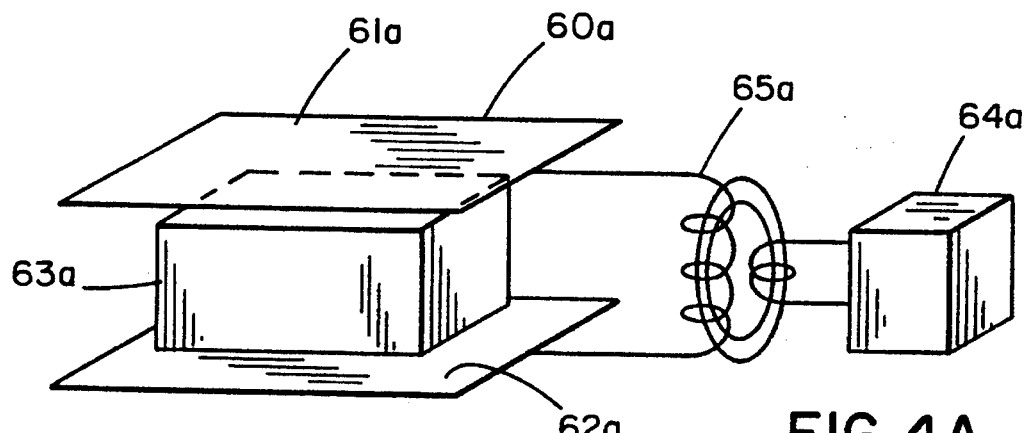
FIGS. 4A, 4B, 4C, and 4D are schematic representations of a radio frequency treatment unit and radio frequency energy source which may be used in the radio frequency treatment of hazardous waste.

FIGS. 4A, 4B, 4C and 4D illustrate the transition from a parallel plate TEM applicator 60 to a controlled limited mode TE or TM applicator. FIG. 4A shows a reactor 60 formed of two parallel plates 61 and 62 with the material 63 placed between the upper and lower plates 61 and 62, respectively. Voltage is applied between the upper and lower plate by means of a tuning coil which is driven from the RF source 64. As long as the wavelength of the applied voltage is large compared to the dimensions of the applicator 60, and the box 63 is well within the extended portions of the metal plates 61, 62, a uniform field can be applied.

Figure 4B:
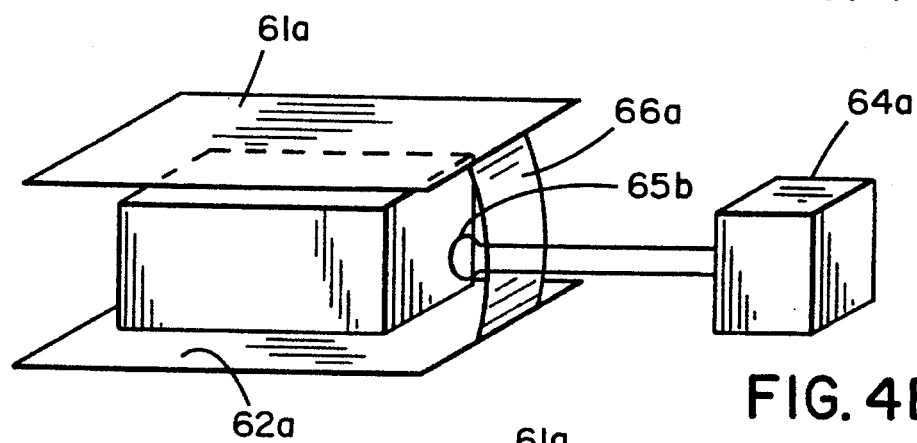
Figure 4C:
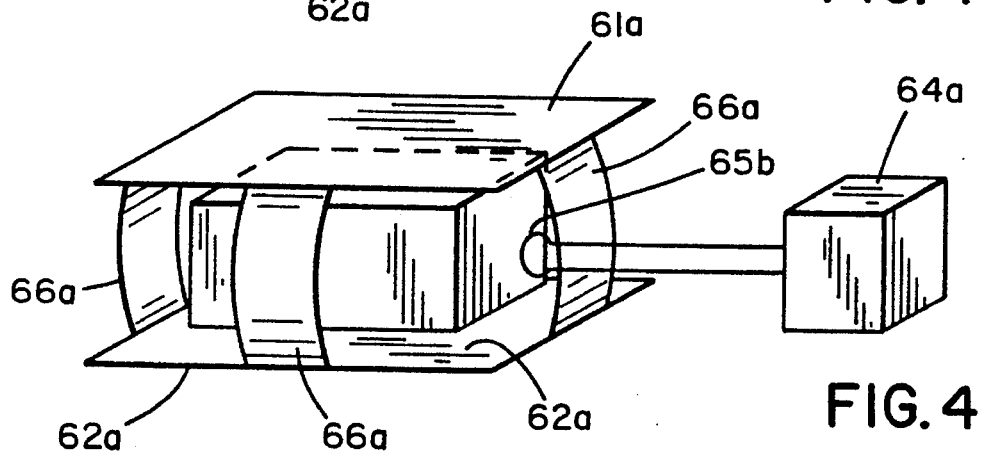
Figure 4D:
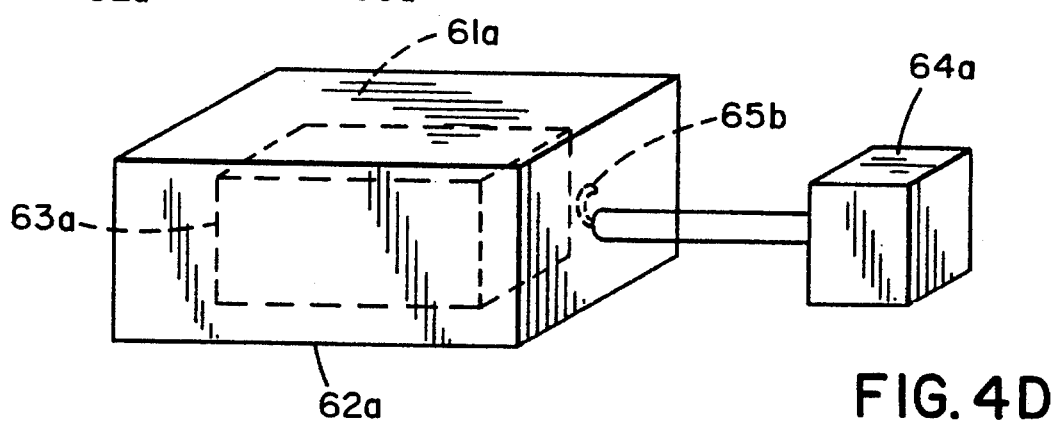

The applicator shown in FIG. 4A is, of course, limited to the lower frequencies, and because the dielectric absorption is roughly proportional to the "nth" power of the frequency (where n ranges from 0.3 to 1.0 for frequencies below the 300 MHz) and the square of the electric field, substantially higher electric intensities for lower frequencies are required to cause the same heating effect (assuming the box nearly fills the available volume) as might be expected for higher frequency operation. Higher frequency operation is possible in a controlled mode heating cavity 60 such as shown in FIG. 4D. The transition of the reactor 60 from the embodiment of FIG. 4A to that shown in FIG. 4D is illustrated in FIGS. 4B and 4C. The parallel plates 61, 62 shown in FIG. 4A are resonated with the thin wire series inductance 65. However, by reducing the value of this inductance, higher frequency resonances are possible. However, there is an upper limit to the frequency at which this resonance can be made to occur if just a single thin wire solenoidal inductor is employed. To increase the resonant frequency, straps 66 on the sides of the two parallel plates 61, 62 can be employed as shown in FIGS. 4B and 4C, with power applied by way of a launching coil or turn 65. Eventually this arrangement is transformed into the controlled TE or TM applicator as shown in FIG. 4D. The controlled TE or TM applicator 60 is defined where ½ wavelength is comparable to the large dimension of the box. This limits the number of permissible modes and allows controlled and uniform heating. In the case of a microwave oven, the dimensions are in the order of 6 to 8 ½ wavelengths, and this results in uncontrolled modes and nonuniform heating.

In the case of the parallel plate exciter, FIG. 4A, the dimensions of the box 63 compared with the dimensions of the electrodes 61, 62 are important in order to assure reasonably uniform electric field and resultant heating effects. To determine the relationship between the box dimensions and the size of the electrode exciter, the data in FIG. 5 were developed. This shows equipotential lines (horizontal) coupled with the displacement current lines (near-vertical) for a limited extent exciter electrodes 61, 62 centrally located in a large conducting box. The relative electric field at any location can be developed by determining the dimensions of a square at any location and a similar square in the uniform region (far right) and dividing the maximum dimensions of this uniform field square by a similar dimension of the square at the desired location.

It can be seen therefore, if the guard distance, that is the distance from the edge of the box to the downward projection of the edge of the electrode, is equal to the height of the electrode, that very little field distortion occurs and that the electric field in the region to the right of this point is reasonably uniform. Further studies show that if the edge of the box is moved farther to the left, field distortion occurs such that the electric field is significantly less near the ground plane and therefore the material of the box would experience a significantly lower heating rate. Guard distances which are equal to about one-fourth or less than the height of the exciter electrode are relatively unsatisfactory.

On the other hand, it is seen that as the height of the box is increased, the field distortion near the edge of the electrode is such as to contribute excess field intensities, particularly where the height of the box is 75% of that of the exciter electrode and the guard distance is equal to one-quarter of the electrode height. Data taken from this plot are summarized in Table 1. It may be seen that guard distances as little as one-fourth the height of the electrode are acceptable but, on the other hand, the maximum height of the box probably should preferably be no more than 67% of the height of the exciter electrode. The reason for this is that as the box enters from the left going into the right, it encounters increasingly high levels of electric field near the edge of the electrode. As a consequence, excess field intensity can occur there which can lead to potential gradients and arcing phenomena. To ensure against such effects as well as over or under heating, the normalized heating rate during entry near the top edge of the box should not vary more than 1.5 to 1.0 for the parallel plate type of the heater shown in FIG. 4A. When the bulk of the water is not evaporated but rather repositioned, heating ratios of 2.0 to 1.0 can be tolerated. When the bulk of the water is evaporated and heating is continued beyond the evaporation point, the heating rate variation should be less than 1.5 to 1.0.

TABLE 1

HEATING POTENTIAL ($E^2$) NORMALIZED TO THE HEATING POTENTIAL IN THE UNIFORM FIELD REGION AS A FUNCTION OF THE BOX HEIGHT RELATIVE TO THE HEIGHT OF THE ELECTRODE AND FOR RELATIVE GUARD LENGTHS.

| Dimensions Relative to Electrode Height, h | | Normalized Heating Potential, ($E^2$) | | |
|---|---|---|---|---|
| Box Height | Guard Length | Top of Box | Bottom of Box | Top of Box During Entry |
| 0.5 | 0.5 | 0.92 | 0.96 | 1.0 |
| 0.5 | 0.25 | 0.92 | 0.88 | 1.0 |
| 0.67 | 0.5 | 1.25 | 0.96 | 1.21 |
| 0.67 | 0.25 | 1.10 | 0.88 | 1.21 |
| 0.75 | 0.5 | 1.44 | 0.96 | 1.8 |
| 0.75 | 0.25 | 1.2 | 0.88 | 1.8 |

Figure 6A:
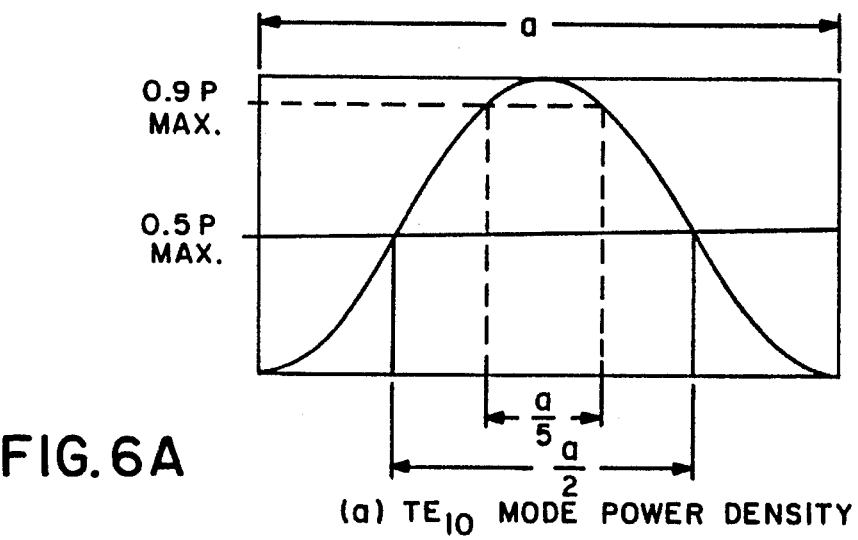
FIGS. 6A, 6B and 6C are graphs of the normalized radio frequency power density in a single end driven radio frequency treatment unit and a radio frequency treatment unit driven at opposite ends by radio frequency energy having two different frequencies to provide uniform average power throughout a major portion of the treating chamber of the unit.
Figure 6B:
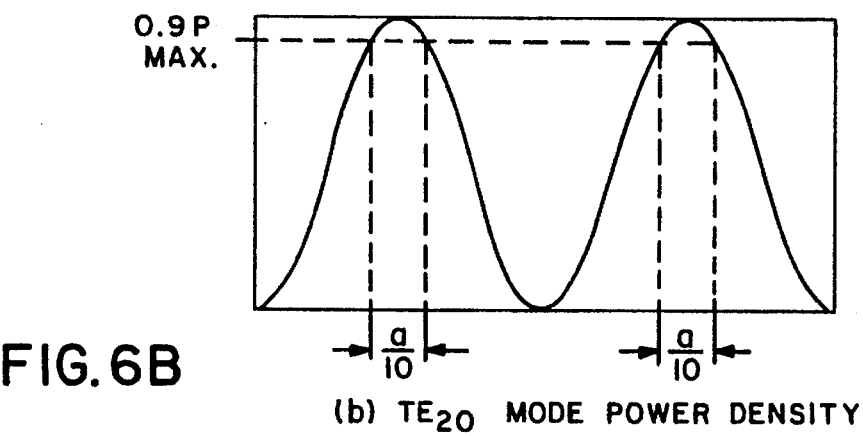
Figure 6C:
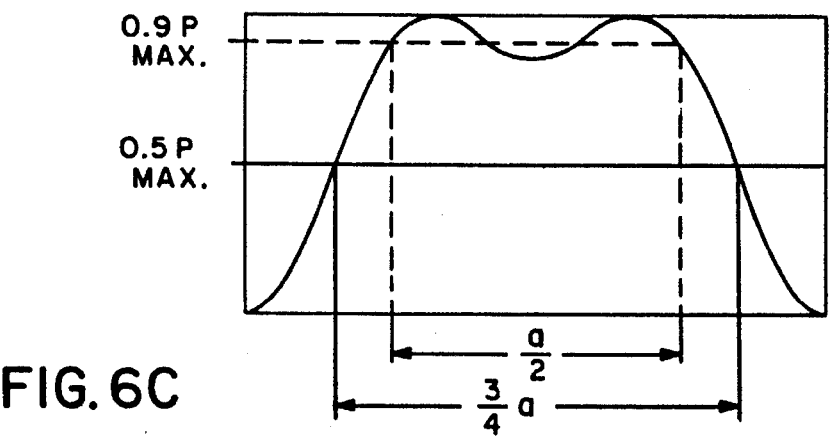
Figure 7A:
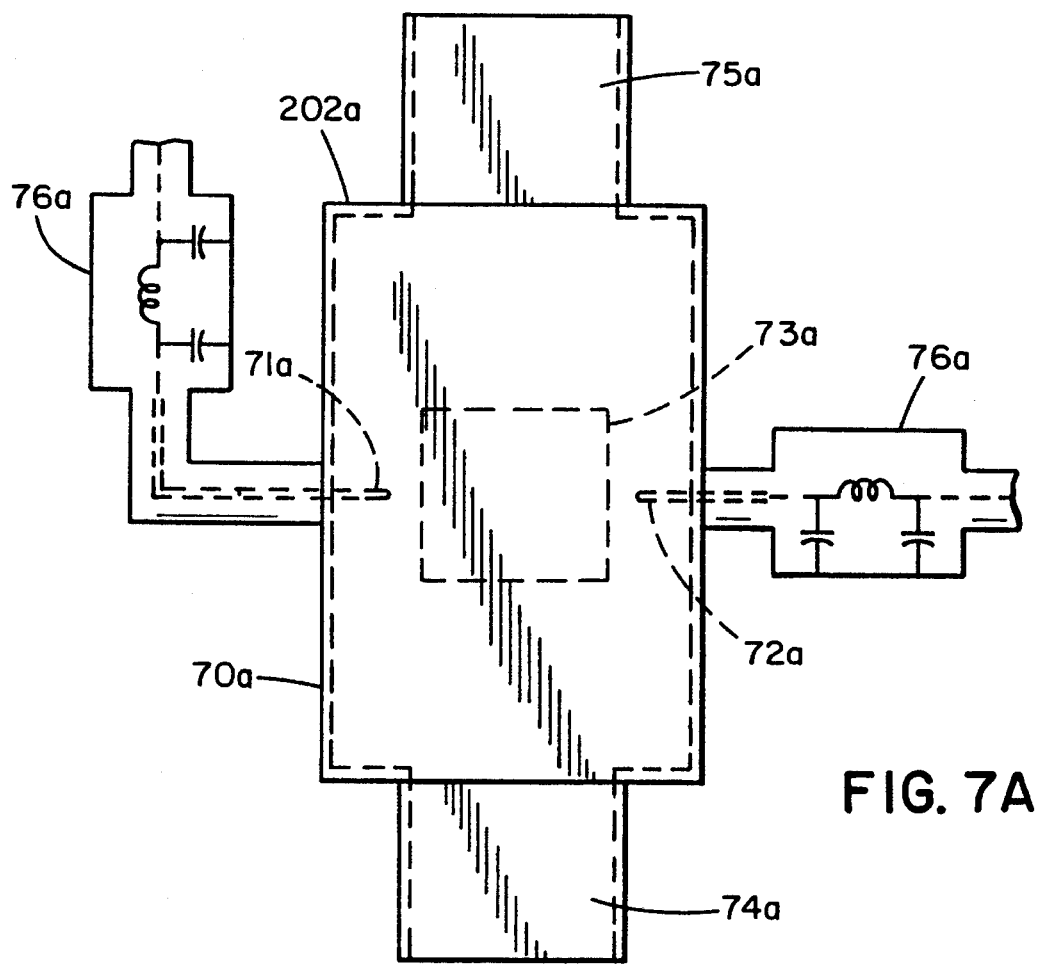
FIGS. 7A, 7B and 7C are elevational views of a radio frequency treatment unit driven at opposite ends by radio frequency energy having two different frequencies.
Figure 7B:
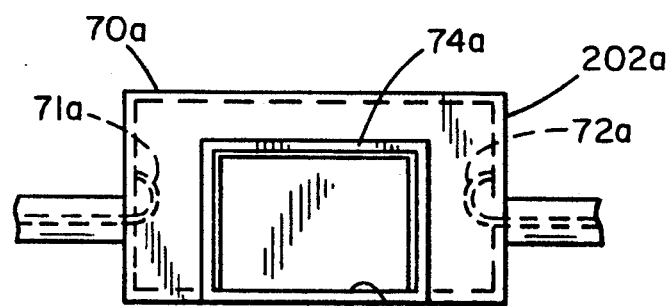
Figure 7C:
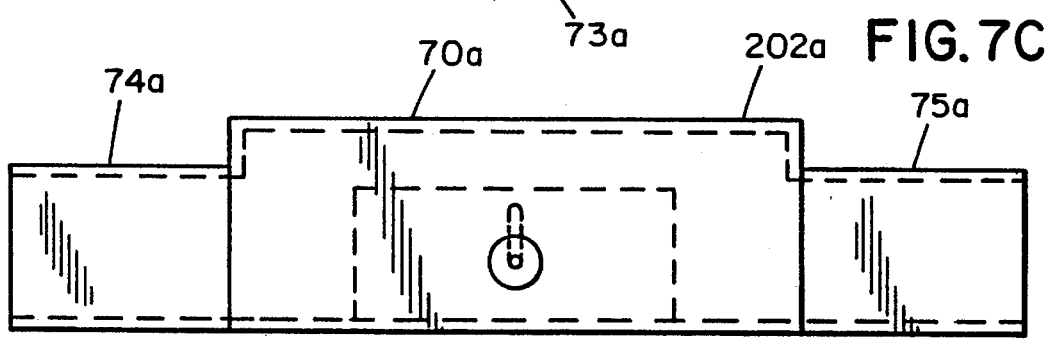

Details of a radio frequency feed structure for the cavity resonator 70 may best be seen in FIGS. 7A, 7B and 7C. The cavity resonator 70 may in an alternative embodiment be fed from opposite sides by loop type exciters 71 and 72. The loop exciter 72 is driven at a frequency of 40.68 megahertz while the loop exciter 71 is driven at twice that frequency, 81.36 megahertz. It may be appreciated that this arrangement allows a highly uniform average power to be present within the cavity. As may best be seen in FIG. 6A, a cavity having standing waves induced therein at the lowest mode, has an average power density with a peak at the center of the cavity. If the cavity is driven at a frequency of 81.36 megahertz a pair of power peaks occur, as may be seen in FIG. 6B. The continued effect of the two feeds of the twin feed cavity shown in FIGS. 7A through 7C is shown in FIG. 6C with the power density curve for a relative amplitude for power of 0.864 at the fundamental 40.68 megahertz frequency and a relative amplitude of 0.48 at the first octave or 81.36 megahertz frequency, thereby providing a highly uniform power across three quarters of the distance across the cavity as shown in FIG. 6C. This further provides uniform heating for the medical waste 63 within the cavity. Waveguide below cutoff entrance 74 and exit 75 allow the waste to be carried into the cavity via a chain mail belt not shown. Matching networks 76 and 77 used to efficiently transfer power from the respective radio frequency sources are not shown. Additional elements of the system are described in FIG. 8 and 9 and include sensor and control systems, wall heaters, and effluent vapor control and treatment.

Figure 8:
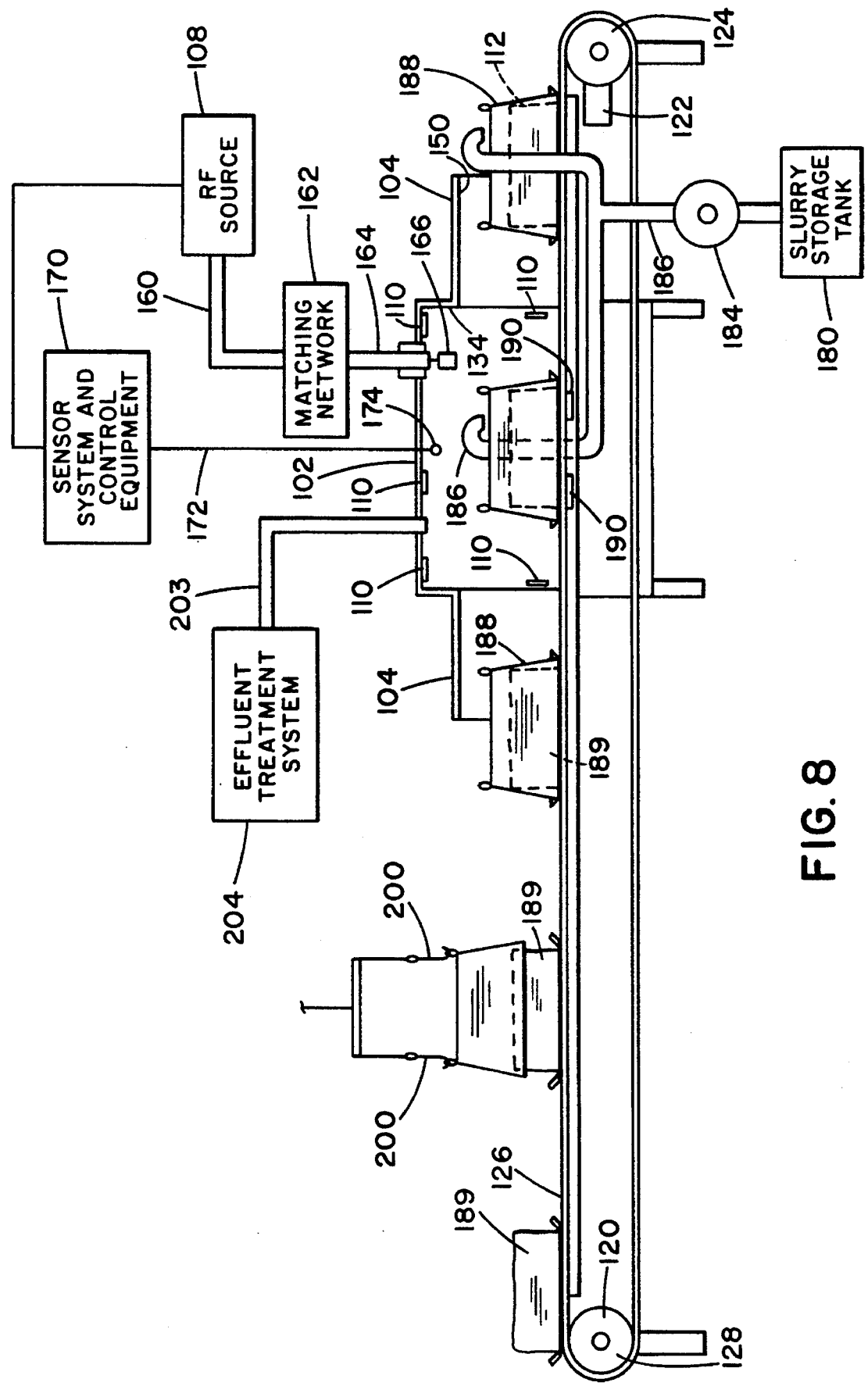
FIG. 8 is a sectional view, shown partially in schematic form, of a drying stage of a slurry treatment system embodying the apparatus of the present invention.
Figure 9:
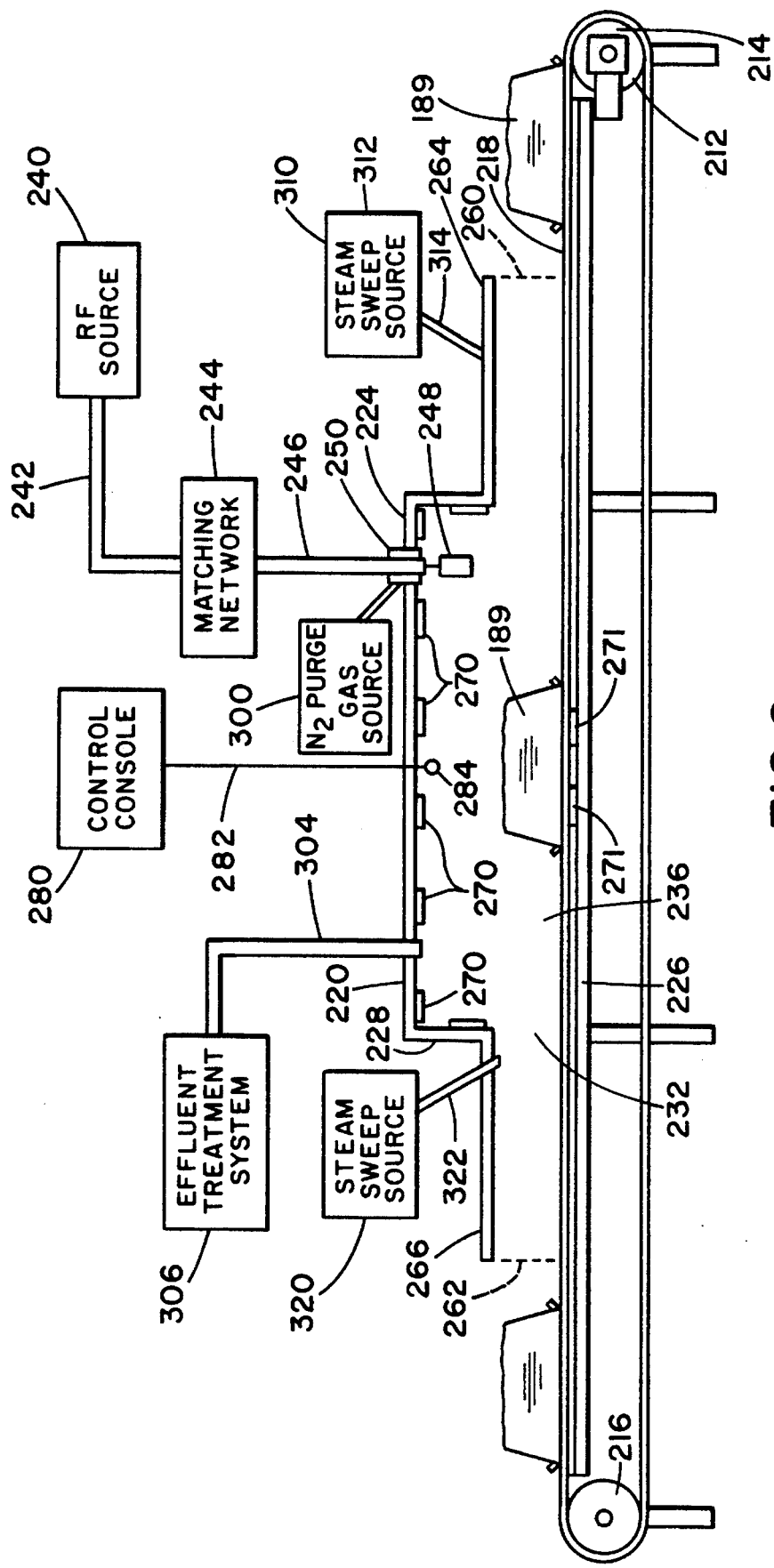
FIG. 9 is a sectional view, partially diagrammatic, of a distillation and pyrolysis stage of a hazardous waste treatment system embodying the present invention.

FIGS. 8 and 9 illustrate a two stage system 100 for the radio frequency treatment of hazardous wastes. Such wastes may include wastes which are biologically or chemically hazardous. The System 100 includes a radio frequency waste treatment reactor or chamber 102 having a wall 104 which defines a waste treatment region 106. Means for energizing the radio frequency waste treatment region comprises a source of radio frequency energy 108 which generates radio frequency energy preferably at a frequency of about 64 megahertz but may also generate radio frequency energy at 18 megahertz or other frequencies as well. Preferably the frequency of the source 108 lies in a range between 500 kilohertz and 600 megahertz. The frequency is selected so that there is adequate penetration of the time-varying electric field of the radio frequency energy into the containers of waste which is to be treated within the treatment region 106.

Also included are a plurality of guard heaters 110 for maintaining the treatment region at a temperature slightly above the temperature of the waste 112 which is being processed. This prevents vapor which has been evolved from the waste 112 from recondensing on cooler parts of the waste or on the wall 104 of the radio frequency treatment chamber 102 and thereby prevents refluxing. This is particularly important because otherwise vapors such as hydrocarbons and halogenated hydrocarbons, as well as water, would be redeposited on the cooler waste. If the wall 104 were not heated, the outer portions of the waste would have a reduced temperature since the waste would be heated to an elevated temperature while the waste near the wall would not. As a result, a temperature differential would exist between the interior of the waste and the waste near the walls, causing the exterior portions of the waste to be inadequately heat-treated and/or causing refluxing of hydrocarbons which may lead to unwanted chemical reactions such as polymerization. The guard heaters 110 are usually embedded in an insulation layer 114. The guard heaters 110 and the insulation layer 114 maintain the interior surface of the wall 104 at least substantially as hot as the waste being treated to prevent evolved vapor from condensing on the interior surface of the wall.

A conveyor 120 carries the waste 112 through the radio frequency treatment region 106. It may be appreciated that the conveyor 120 may be operated continuously or semi-continuously; that is, it may feed the waste 112 continuously through the reactor 102 while the reactor 102 is energized, or may move packages into the reactor, halt movement while the waste is being heated by the radio frequency field and then move the waste out of the reactor after it has been treated.

The conveyor 120 includes a motor 122 connected to a roll 124 which frictionally engages a conveyor belt 126. A roll 128 also frictionally engages the belt. The rolls 128 and 124 drive the belt so that the waste 112 can be conveyed through the radio frequency reactor 102.

The radio frequency reactor 102 is generally rectangular, having a plurality of walls including a top wall 130, a bottom wall 132, a first end wall 134, a second end wall 136, a first side wall 138 and a second side wall 140. There is an inlet opening 150 in the end wall 134 and an outlet opening 152 in the end wall 136. A waveguide 154 dimensioned to be below the cutoff frequency limit of the radiation generated by the radio frequency source 108 is connected to the wall 134 at the inlet opening 150. Similarly, a waveguide below cutoff 156 is connected to the wall 136 at the outlet opening 152. The waveguides 154 and 156 comprise tunnels which allow the waste 112 to be conveyed through the waveguides and into and out of the treatment region 106, without the necessity of using doors and the like to keep the radio frequency radiation from leaking out of the chamber 102. However, doors may also be used to enclose the waveguides 154 and 156, effectively sealing the radio frequency chamber 102 to keep any vapor or effluent which may be evolved from the waste from being inadvertently released to the environment.

The source of radio frequency energy 108 is connected a coaxial cable 160 which feeds the energy to a matching network 162. After exiting the matching network, the energy flows down a coaxial cable 164 to an exciter loop 166 positioned within the treatment region 106 where, when excited by radio frequency energy, it creates a time-varying electric field within the treatment region 106 for the radio frequency heating of the waste 112.

A sensor system 170 for sensing electric field strength and for the temperature within the treatment region 106 is connected by a lead 172 to a sensor 174 positioned within the treatment region 106.

The waste may take the form of a slurry which is stored in a slurry storage tank 180 fed by a pipe 182 to a pump 184, and delivered by a delivery pipe 186 to a tank 188 which comprises a material made of plastic or the like which is substantially transparent to the radio frequency energy, for instance, 64 megahertz. The slurry is pumped into the tank 188 either outside the chamber 102 or inside the chamber and, in any event, placed inside the treatment region 106 for exposure to radio frequency energy. An ohmic heating element 190 may be positioned within the radio frequency treatment chamber to heat bottom portions of the tank containing metal to offset any conductive or convective heat losses. The material is heated sufficiently to drive off water and possibly other vapors and after heating is completed, the dried residue 192 in the tank 188 is moved out of the radio frequency treatment chamber 102 by the conveyor belt 126. After being so removed, the residue may be partially solidified and a portion of the tank 188 may be lifted by hooks 200 away from the dried slurry which is then left behind as a briquette 189.

The briquette 189 is then fed to a distillation and pyrolysis system 210 as may best be seen in FIG. 9. The distillation and pyrolysis system 210 includes a conveyor 212 having a roll 214, a roll 216 and a conveyor belt 218 engaging the rolls 214 and 216 for moving the briquette 188 through a treatment region. The conveyor 212 comprises a means for continuously passing waste through the waste treatment region and may be driven by a motor coupled to one of the rolls 214, 216. A radio frequency treatment unit 220 comprises a radio frequency treatment chamber 222 having a top wall 224, a bottom wall 226, a first end wall 228, a second end wall 230, a first side wall 232 and a second side wall 234 defining a substantially rectangular treatment region 236. The briquettes 189 of waste material are moved through the chamber 222 by the conveyor 212.

A source of radio frequency energy 240 is connected by a coaxial cable 242 to a matching network 244 to energize a coaxial cable 246 with radio frequency energy and drive a loop exciter 248 positioned within the radio frequency waste treatment region 236. A dielectric plug 250 seals the cable entrance through the top wall 224. The side wall 230 has an inlet opening 260 formed therein. The side wall 228 has an outlet opening 262 formed therein. A waveguide below cutoff 264 is positioned as an inlet tunnel flush with the inlet opening 260, and a waveguide below cutoff 266 comprising an exit tunnel is positioned flush with the outlet opening 262. A plurality of guard or wall heaters 270 are mounted on the top wall 224 to maintain the interior region 236 substantially isothermal to prevent vapor which may be evolved from the briquette 188 from recondensing on the briquette or condensing on the walls of the treatment region 236. This prevents unwanted polymerization and other reactions within the treatment region.

When driven by the radio frequency source 240, the exciter loop 248 creates a electromagnetic field within the treatment region 236, and in particular, produces a 64 megahertz time-varying electric field which heats the briquette 189.

Figure 5:
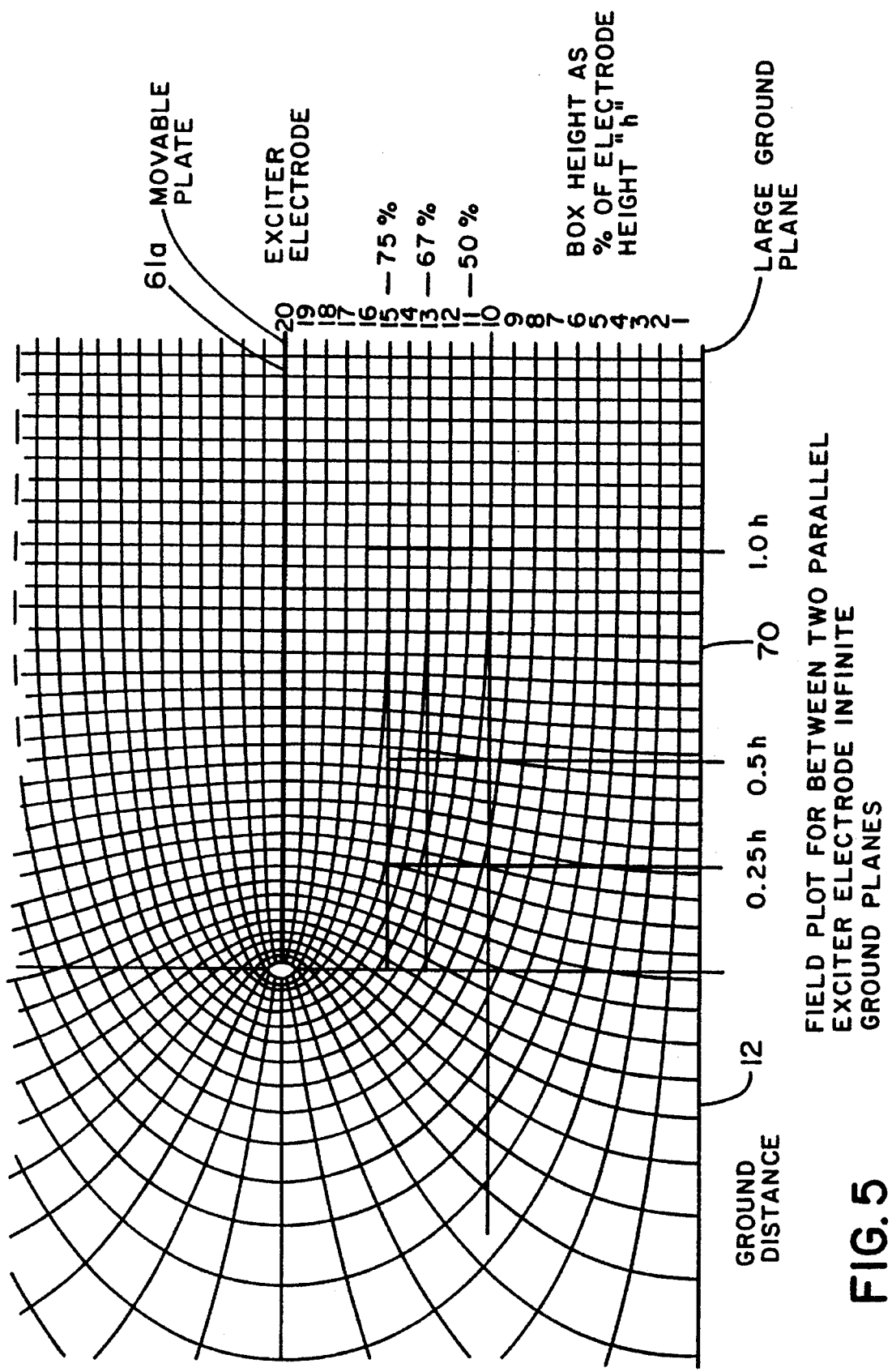
FIG. 5 is a section of a radio frequency reactor showing the electric field vector lines and equipotential lines generated within a radio frequency treatment unit.

In other embodiments, an 18 megahertz time-varying electric field parallel plate exciter, FIG. 4A, may be used or any suitable frequency between 500 kilohertz and 600 megahertz. However, the cavity type exciters (FIGS. 4A, 6 and 7) are preferred to heat the briquette or other material above 105° C. since higher field intensities must be used to offset the lower conductivity expected at the higher temperatures. The cavity does not enhance the field intensities as does the parallel plate as shown in FIG. 5 near the edge of the exciter plate, thereby reducing arcing.

A monitor 280 connected by a lead 282 to sensors 284 positioned within the treatment region 236 provides indications of the temperature, hydrocarbon concentration electric field strength and the like within the treatment region 236 to determine when the radio frequency energy should be interrupted or when the briquette 189 should be moved out of the treatment region by the conveyor 212. Since vapors, including hydrocarbons, halogenated carbons and possibly pathogens, may be evolved from the briquette 189, it is important that they be safely removed from the treatment region 236. In order to remove them, a source of nitrogen gas 300 is connected via a line 302 to empty into the treatment region 236. The nitrogen gas may be removed by a duct 304 which is connected to a fluid effluent treatment system 306. Further, in order to help remove certain noxious materials from the briquette 189, a steam stripping system 310 may be supplied with a source of steam 312 feeding a duct 314 connected to the inlet tunnel 264. The steam may be used to flood the treatment region 236 and aid in removing hazardous or noxious compounds from the briquette 188. A second steam sweep source 320 may be connected by a duct 322 to the exit tunnel 266 to aid in preventing noxious materials from reaching the environment. Alternatively, the sweep could be injected below the briquette and recovered just above the briquette.

The descriptions provided herein in describing FIGS. 8 and 9 teach the application of the current invention for sequential removal of water and organics in two different systems. It is within the scope of the present invention to simultaneously remove water and organics using a simple processing step as described in FIG. 3

Figure 10:
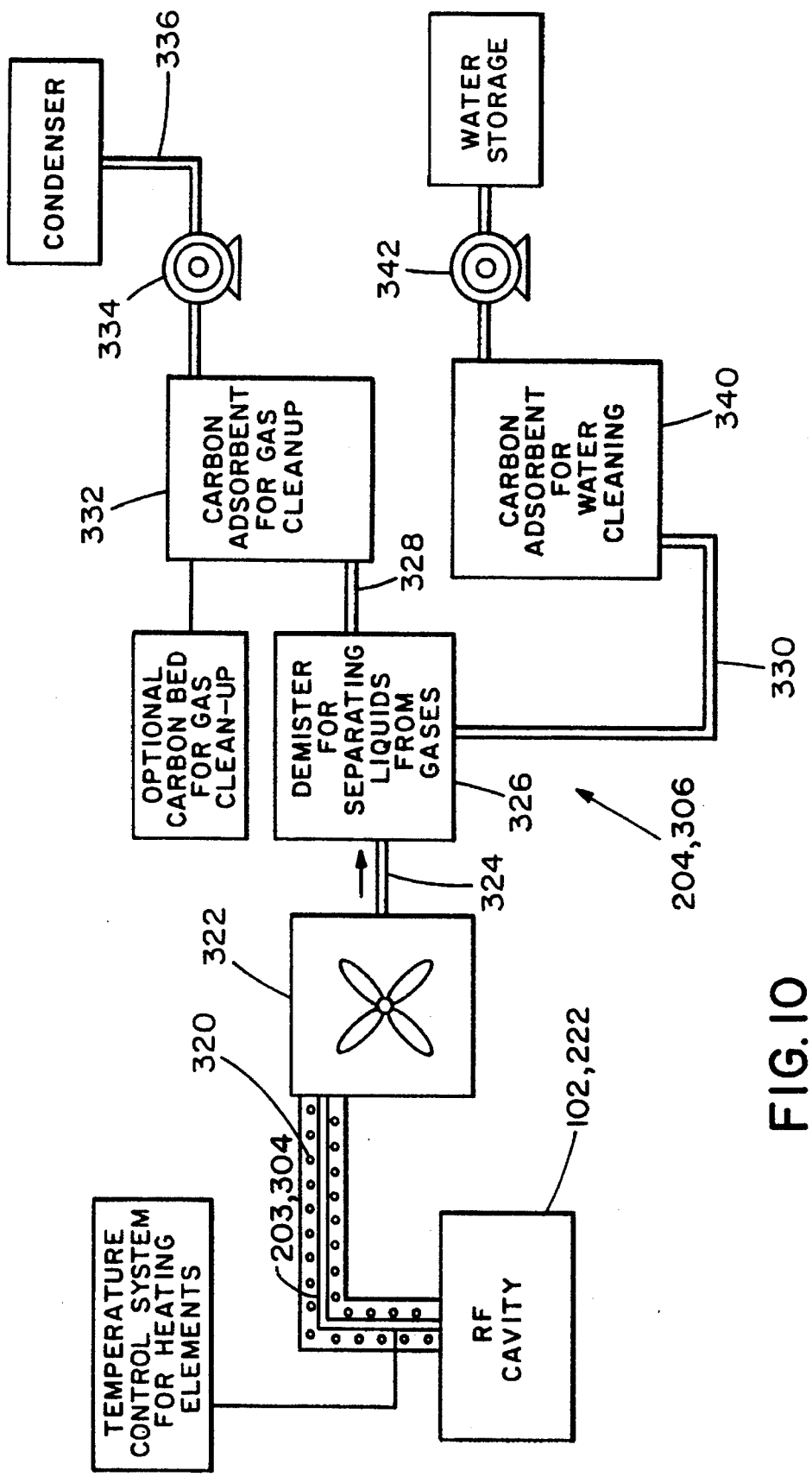
FIG. 10 shows a vapor treatment system employing condensation and treatment of effluent evolved from the treatment of hazardous waste in accordance with the present invention.
Figure 11:
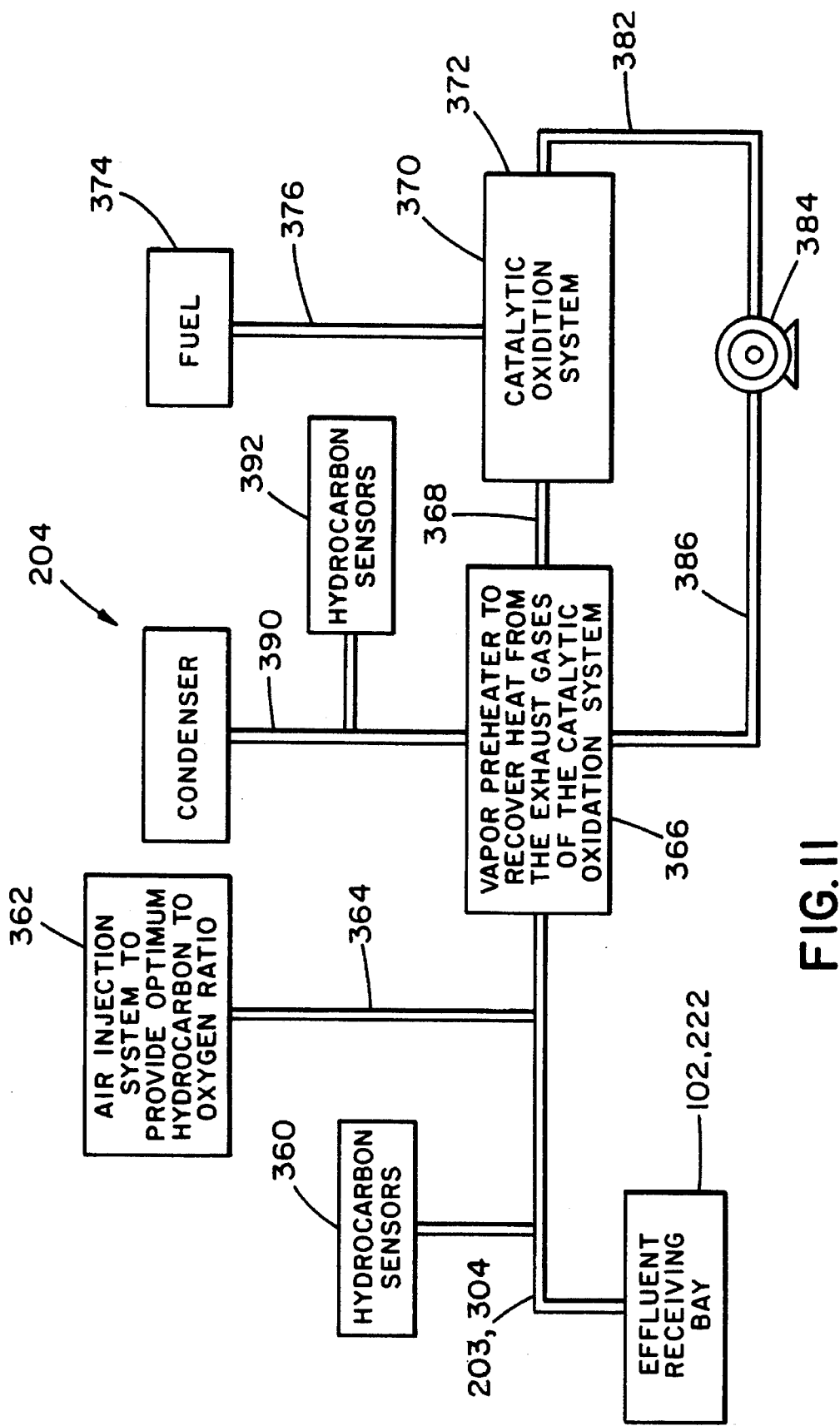
FIG. 11 shows a vapor treatment system employing catalytic oxidation of effluent generated from hazardous waste.

The vapor treatment system 204 and the vapor treatment system 306 may be identical, a first embodiment shown in FIG. 10, and a second embodiment shown in FIG. 11. Referring now to FIG. 10, the radio frequency treatment chamber 102, or in the alternative, the radio frequency treatment chamber 220, is connected to the duct 203, 304 which includes a heater 320 to prevent water vapor or other vapors from condensing within the duct. The duct 203, 304 feeds an air cooled heat exchanger 322, which, after reducing the temperature of the vapors, feeds the resulting fluid stream through a duct 324 to a fluid gas separator 326, which in this embodiment is a demister. The demister 326 separates any remaining gas into a gaseous fraction which is fed on a gas fraction line 328, and a liquid fraction which is fed on a liquid fraction line 330. The gas fraction line 328 is connected to gas bead adsorber 332 containing activated carbon which removes any harmful constituents and allows pure nitrogen to be vented by a blower 334 through a duct 336 to the environment. A liquid adsorber 340 is connected to the line 330, and adsorbs any organic fractions and the like. Clear water is then drawn off by a pump 342 and fed to a storage tank or the like for disposal. This vapor treatment system is based on condensation principles.

In the alternative, a vapor treatment system based on catalytic oxidation may be used as may best be seen in FIG. 11. That system is connected to the radio frequency cavity 102 or 220 by the duct 203 or 304 to which is connected a hydrocarbon sensor 360. A source 362 of air for aiding in combustion is connected via a duct 364 to the line 203, 304. A heat exchanger 366 receives the vapors from the line 203, 304 and causes them to be heated by exhaust vapors from the system as will be seen hereinafter. The vapors are fed by a line 368 to a catalytic oxidizer 370 having Torvex catalyst 372 packed therein. Fuel such as natural gas, propane or the like from a source 374 may be fed optionally via a duct 376 to aid in the catalytic combustion of the materials. Exhaust gases are released through an exhaust gas duct 382 which is connected to a blower 384, which feeds pressurized exhaust gases through a duct 386 into the heat exchanger 366 where they transfer heat to the gases in the duct 203. The gases in the duct 386 are cooled by the heat transfer, and the cooled gases comprising carbon dioxide, water vapor and nitrogen as well as air are vented through a vent duct 390 to the environment. A hydrocarbon sensor 392 is connected to the vent duct 390 to determine whether the gases contained any uncombusted hydrocarbons.

Figure 12A:
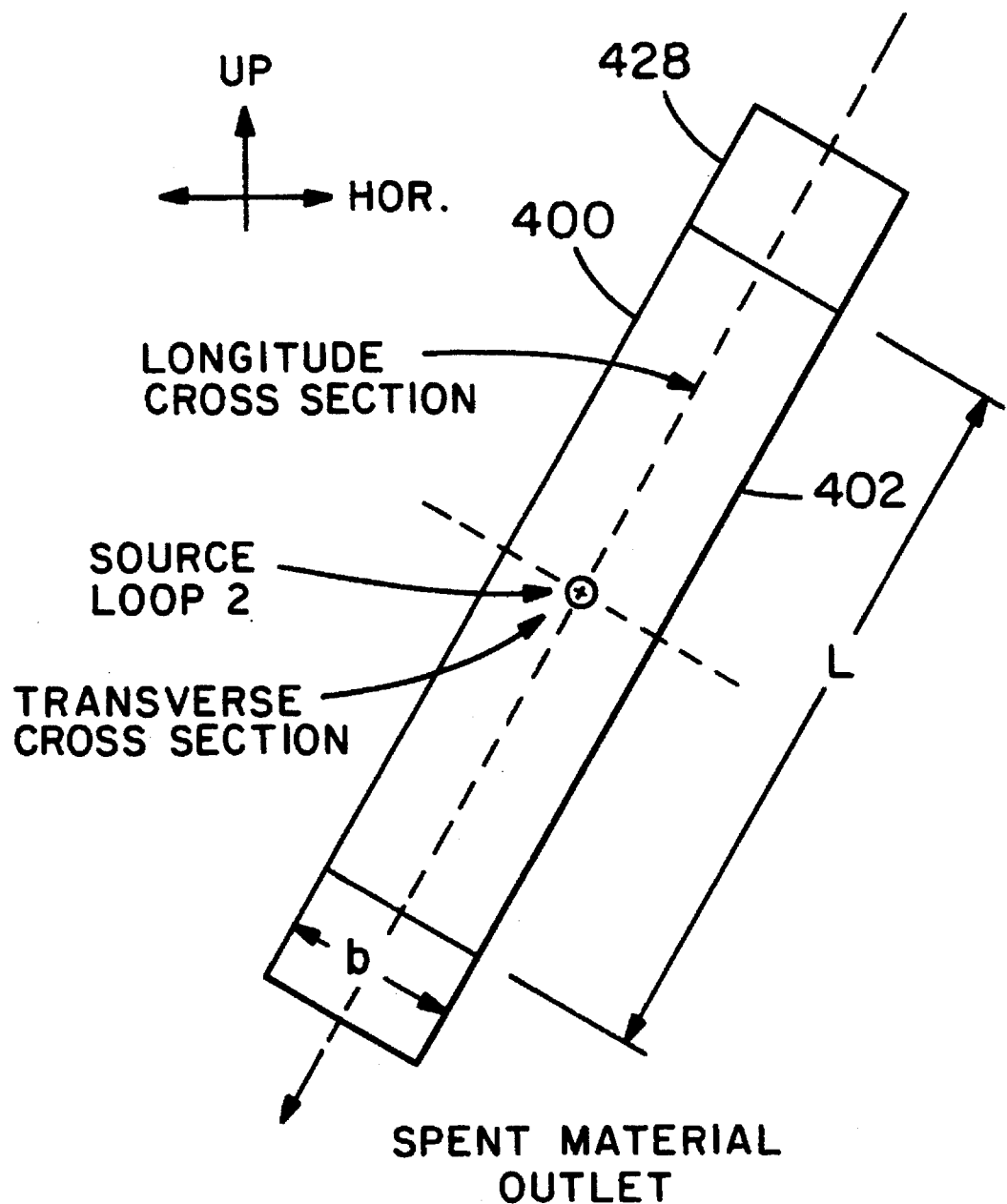
FIG. 12A is an elevational view of a radio frequency treatment unit comprising an inclined filled waveguide.
Figure 12B:
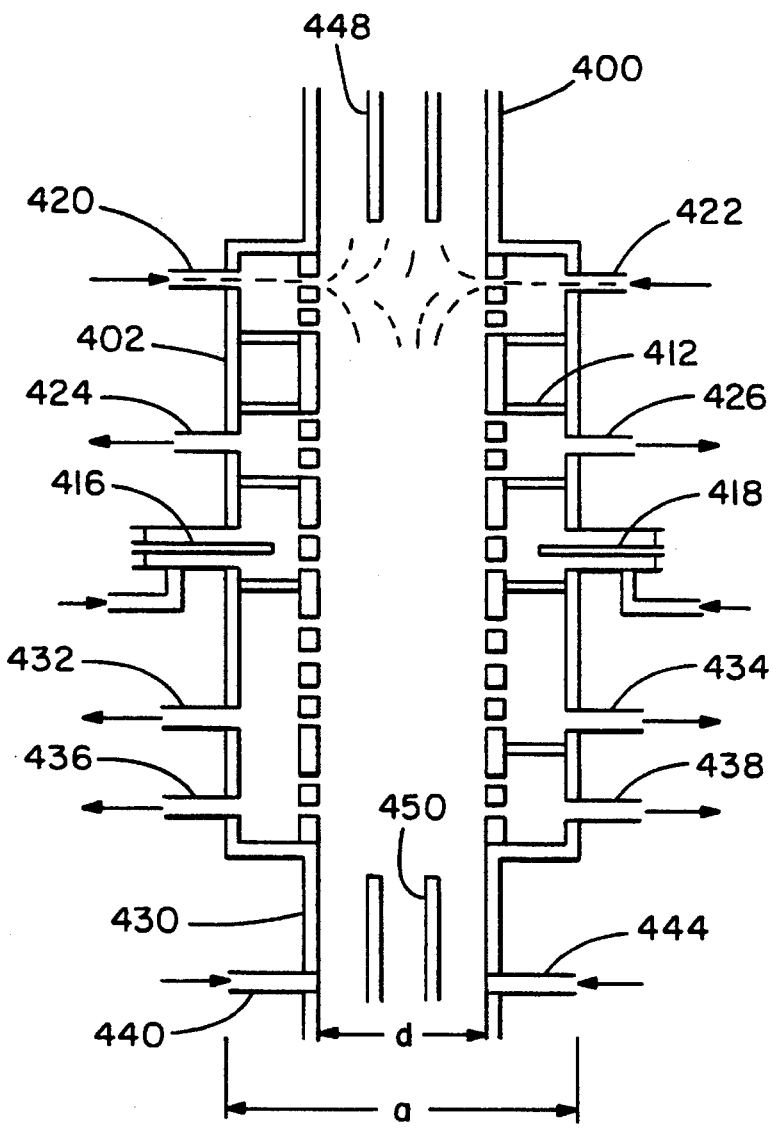
FIG. 12B is a longitudinal sectional view of the radio frequency treatment unit shown in FIG. 12A.
Figure 12C:
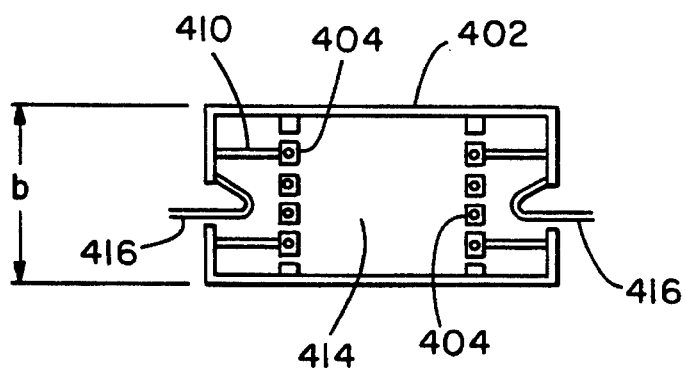
FIG. 12C is a transverse sectional view of the radio frequency treatment unit shown in FIG. 12A, taken along line 12C—12C in FIG. 12B.
Figure 13:
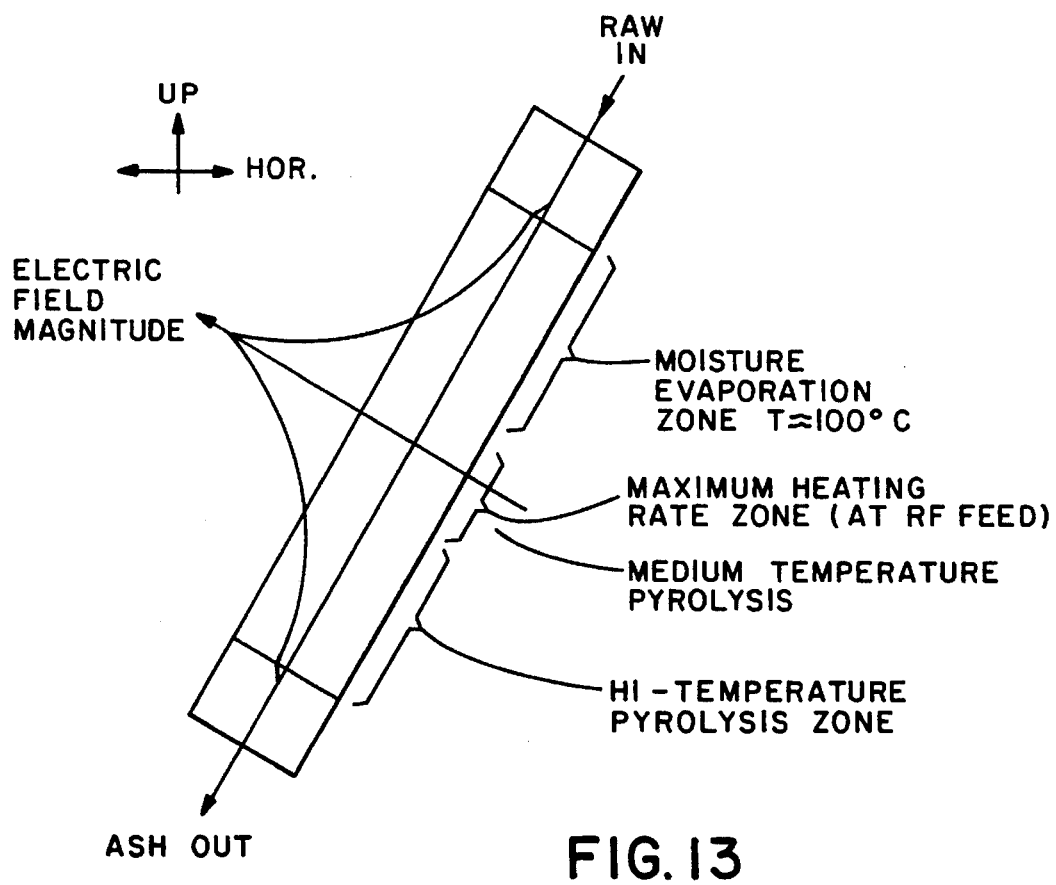
FIG. 13 is an elevational view of the radio frequency treatment unit of FIG. 12A with a graphical representation of the electric field magnitude within the unit.

In an alternative embodiment of the system, a tilted kiln 400 as shown in FIGS. 12A, 12B and 12C, may provide the radio frequency treatment chamber. The tilted kiln 400 is formed with a cross section 402 bounded in part by a perforated ceramic wall 404. The perforated ceramic wall has a plurality of cooling tubes 410 running therethrough for preventing overheating of the perforated ceramic wall. The ceramic wall is suspended from an exterior wall 411 by a plurality of struts 412. The interior of the kiln 400 includes a treatment region 414 which is defined substantially by the metal walls 403 and the ceramic walls 404. The treatment region 414 is excited by radio frequency energy from source loops 416 and 418. The loops may be driven at different frequencies to provide more uniform heating within the kiln. FIG. 13 describes the longitudinal distribution of the electric field on the assumption that the energy is almost absorbed as it propagates along the $TE_{01}/TE_{02}$ waveguide. The transverse field distributions are similar to that shown in FIG. 6 as discussed for the arrangements shown in FIGS. 6 and 7. As may also be seen, inlets 420 and 422 are provided for feeding steam for stripping into the treatment region 404. Low temperature vapor lines 424 and 426 are positioned near the feed end 428 of the tube through which the waste 12 enters for treatment.

The material is progressively heated as it falls down the inclined tube drawn by the force of gravity which provides the driving force via the inclination of the tube, for transporting the waste material through the treatment region. The low temperature vapors may include very light hydrocarbons fractions and the like which are drawn off through the low temperature vents 424, 426. In addition, guard heaters may be provided in the metal outer walls to maintain the walls substantially at the temperature of the material as it is passing through. The walls are also progressively heated to higher temperatures as the material travels toward the exit 430 of the system. Further taps 432, 434, 436 and 438 are provided for drawing off vapors having differing vapor pressures so that, in effect, fractionation of the vapors is provided which allows the vapors to be separated by boiling point and to be reused for other purposes. Steam injection ports 440 and 444 are provided at the exit end 440 of the unit. A feed tube 448 and an exit tube 450 are also provided which comprise waveguides below cutoff so that the treatment region 414 can be continuously fed with waste 12 while the treatment region 414 is excited by the radio frequency energy. It may be appreciated that the unit may be excited with 40 or 80 megahertz radio frequency energy or any suitable frequency between 500 kilohertz and 600 megahertz. Thus, the interior of the kiln 400 comprises a cavity resonator for the radio frequency heating of the waste material therein.

Figure 14B:
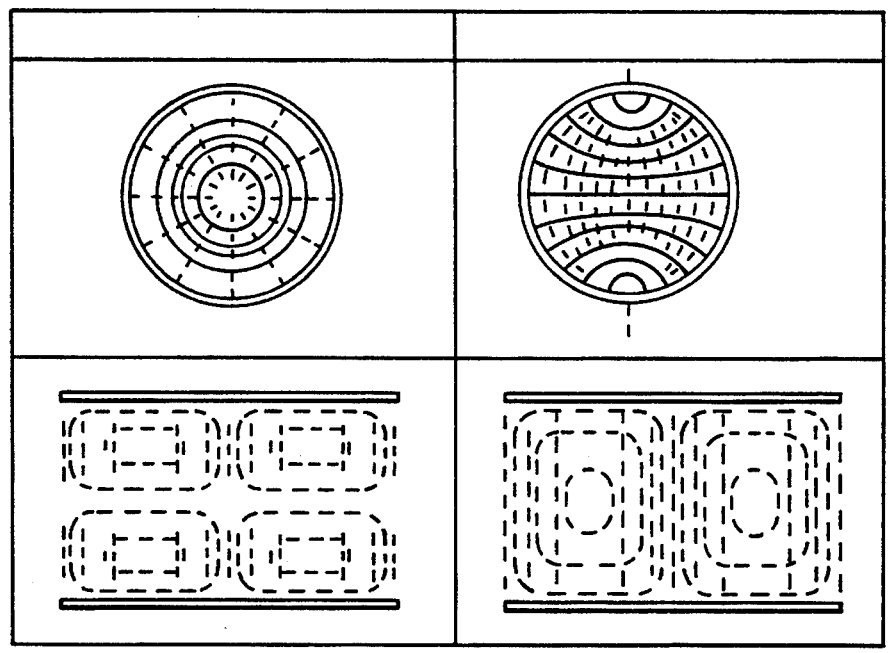
FIGS. 14A and 14B are isometric view having portions broken away showing details of a radio frequency treatment unit for treating hazardous waste embodying the present invention.
Figure 14A:
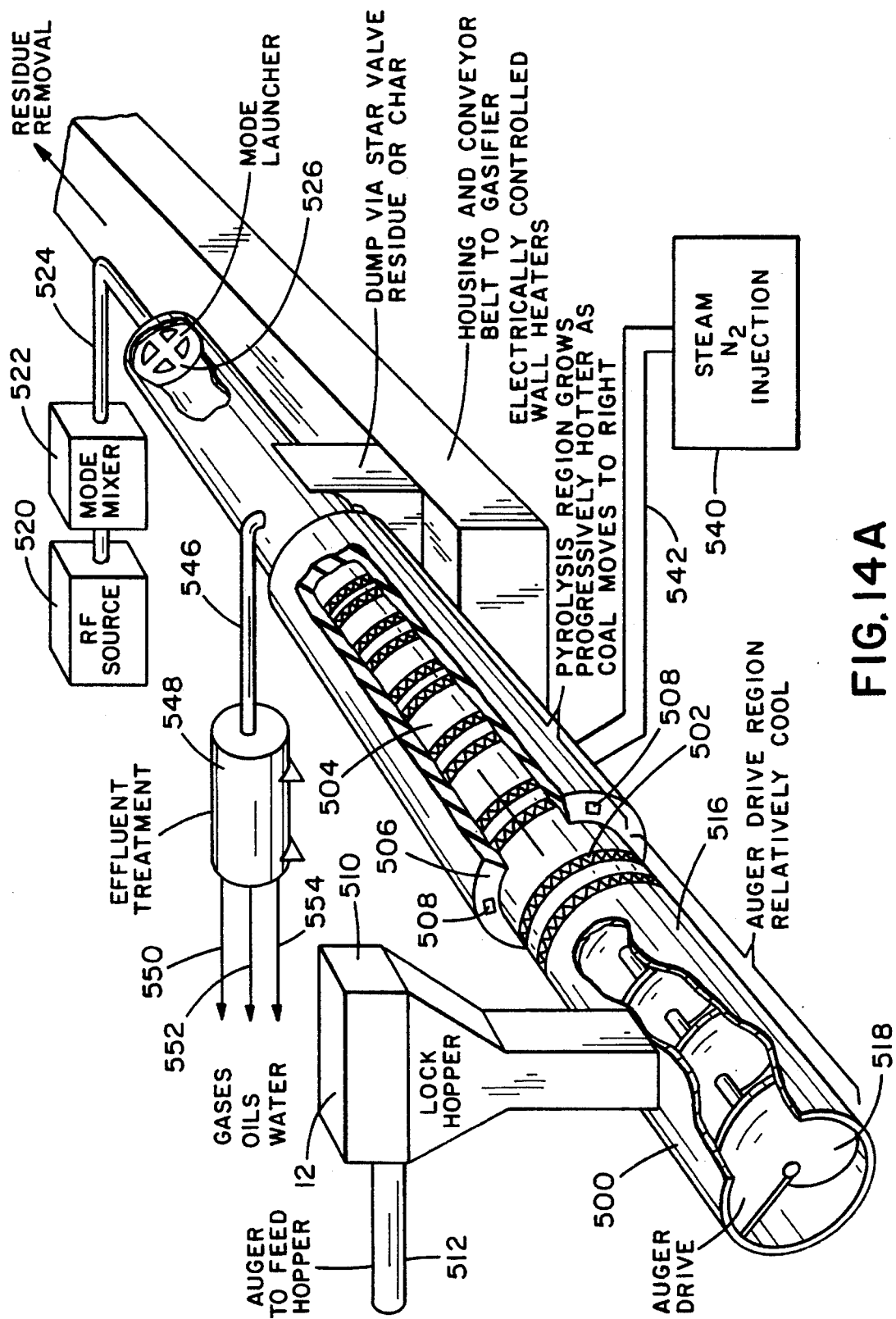

Referring now to FIG. 14, a still further alternative embodiment of the invention is shown therein, in particular, an apparatus 500 includes a radio frequency treating chamber 502, which is substantially circular in cross section, having a radio frequency treatment region 504 defined therein. That region 504 is surrounded by an insulation layer 506, having guard heaters 508 positioned therein. The insulation 506 and the guard heaters 508 prevent unwanted condensation of vapors from the waste material within the treatment region. Waste material 12 is positioned in a feed hopper 510 which is fed by a feed line 512 from a suitable source. The hopper empties into a feed tube 516 in which is positioned an auger 518 comprising a means for continuously moving waste 12 through the treatment region 504. A source of radio frequency energy 520 is connected to a mode mixer 522 which supplies the radio frequency energy through a coaxial cable 524 to a mode launcher 526, which propagates the radio frequency energy down the cylinder 502 in either of the TE01 or TE11 modes, or in a combination of the two to provide mode mixing and uniform heating of the material therein. A gas injection system 540 injects steam or nitrogen gas through a line 542 which is connected to the treatment region 504. Vapors evolved from the waste 12, which may include halogenated hydrocarbons, oils and water, are fed through a vapor outlet line 546 to an effluent treatment system 548, which separates the material into gases fed out by a gas line 550, oils fed out by a oil line 552, and water fed out by a water line 554.

Figure 15:
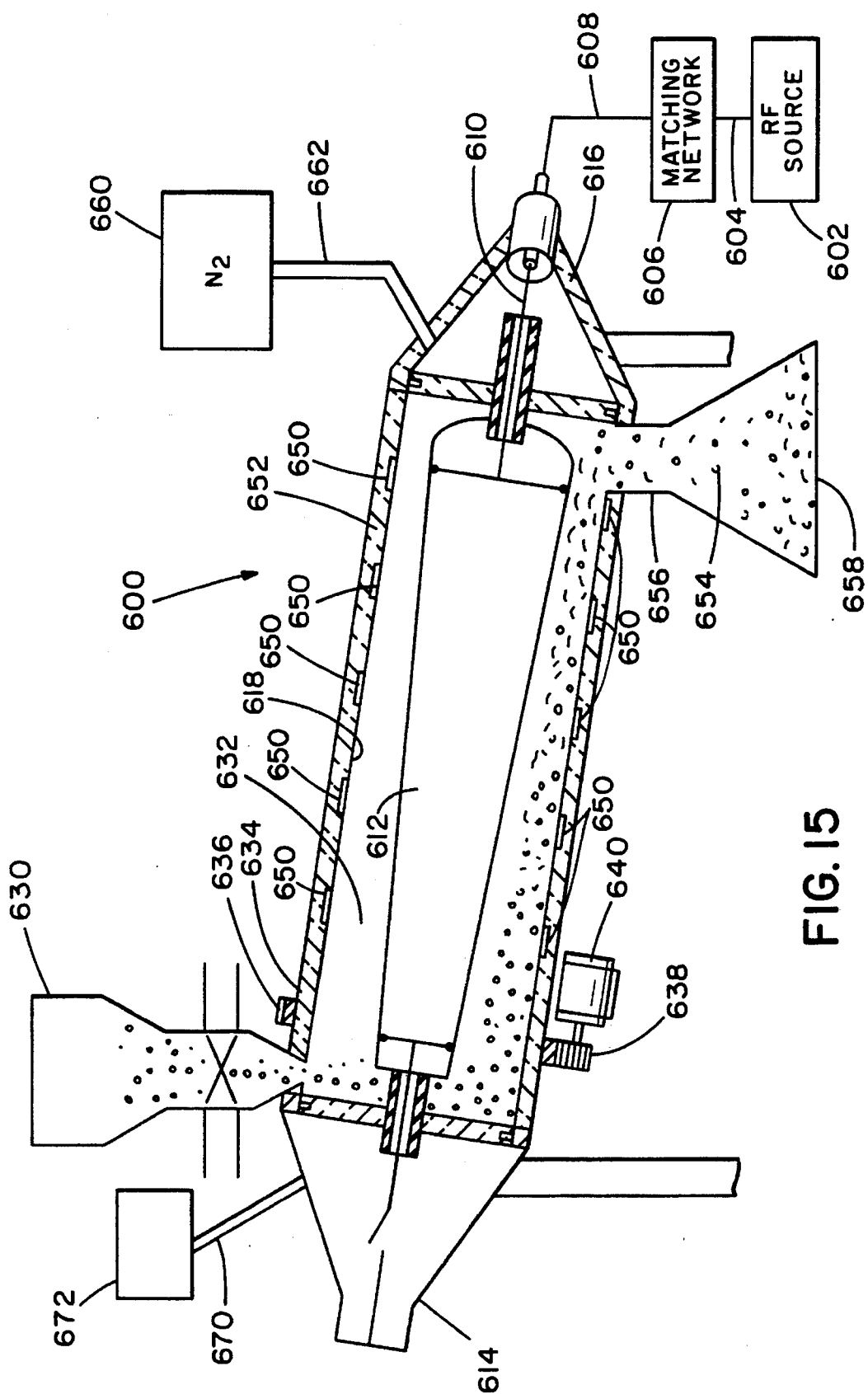
FIG. 15 is a sectional view of a radio frequency treatment unit comprising a transverse TEM mode rotary kiln.

As shows in FIG. 15, a still further embodiment of the instant invention comprises a rotary kiln. The system includes a source of radio frequency energy 602 which feeds a coaxial cable 604 connected to a matching network 606. Power is supplied over a coaxial cable 608 to energize a center line cable 610 for purposes as will be seen hereinafter. The center line cable 610 is connected to a graded diameter cylindrical electrode 612, whose diameter increases as the length of kiln 600 is traversed from an end 614 to an end 616. The kiln 600 also includes an outer electrode 618 which is of substantially constant diameter with a circular cross section. It may be appreciated that normally with matched cylindrical electrodes the electric field would attenuate with increasing distance from the electrode 612 as the space from 612 through 618 is traversed. Alternatively, if the longitudinal absorption is small, grading the electrode can also be used to match the heating rate with the moisture content or conductivity. Further, energy would be adsorbed as one moves away from the inlet end 614 of the kiln. However, the graded electrode compensates for this.

A hopper 630 is fed with waste 12 or other particulate materials, such as coal, to be processed. The particulate material 12 is fed to an interior chamber 632 of the kiln. The kiln includes a wall 634 carrying a cog 636 which is driven by a gear 638, in turn driven by a motor 640, causing the kiln to rotate about the center axis or axis of symmetry. A plurality of guard heaters 650 are embedded in insulation 652 surrounding the kiln wall electrode 618 to prevent heat from leaking out of the system, and to prevent vapors which may be generated by the radio frequency heating of the material 12 from recondensing on the material. Thus, the material is heated by the radio frequency energy and the dried residue 654 resulting therefrom is fed through an output line 656 to a container 658 where it is held for further processing or disposal.

The system also includes a source of nitrogen gas 660 which is connected to a duct 662 and feeds the kiln 600 to remove the vapors therefrom. An outlet duct 670 is connected to a vapor treatment system or effluent treatment system 672. Thus, the radio frequency energy is injected at the end 616, and the field strength increases as the inside electrode 612 tapers toward the inlet end. Furthermore, in order to obtain uniform heating of the waste 12, the motor 640 drives the kiln so that it is rotated to tumble the waste materials to obtain good mixing and uniform heating.

Figure 16:
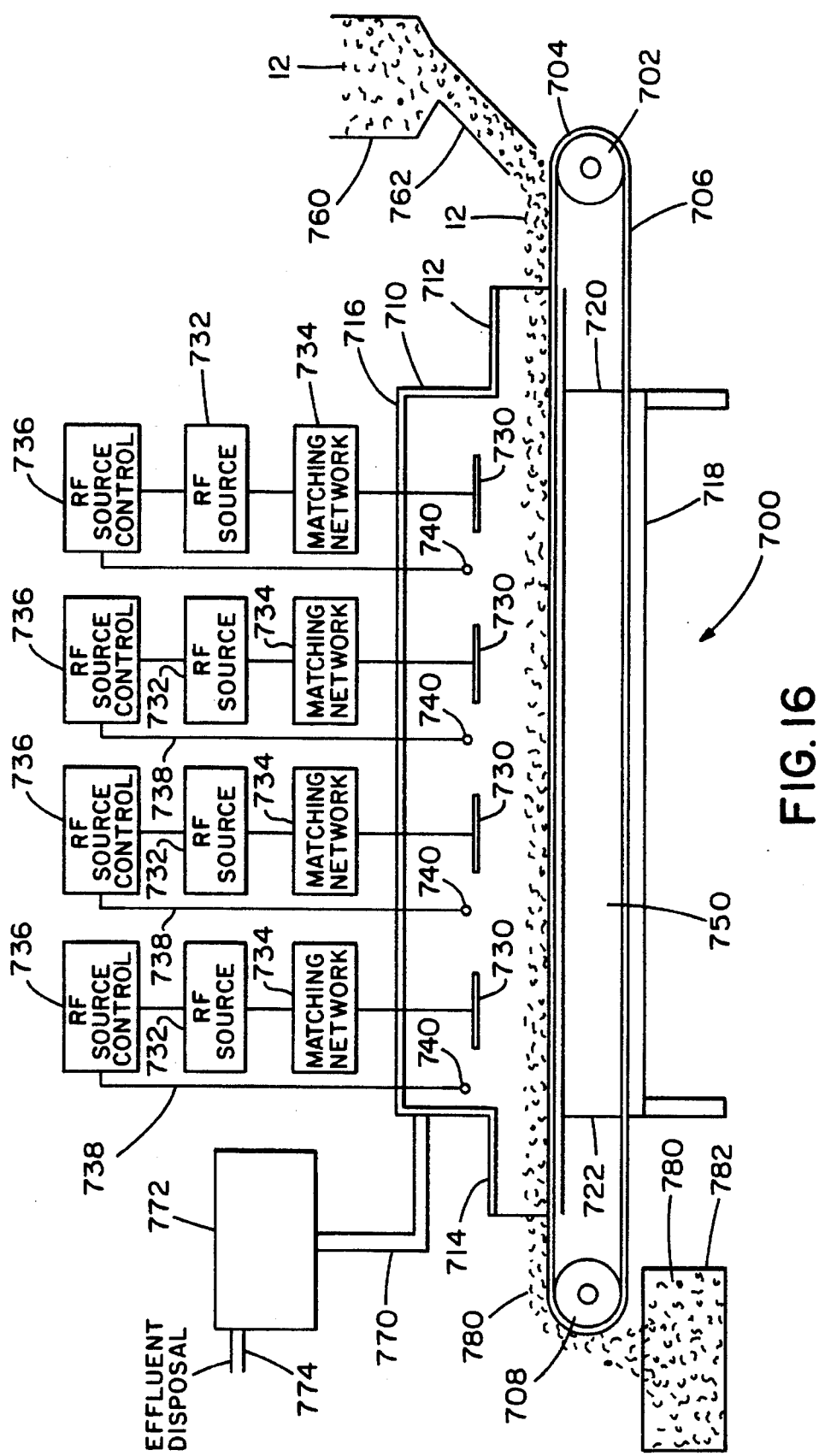
FIG. 16 is a view, partially diagrammatic, of a radio frequency treatment unit employing a plurality of moveable exciter plates therein for treating hazardous.

As shown in FIG. 16, a parallel plate radio frequency treatment system 700 for the radio frequency treatment of waste 12 or other particular matter such as coal includes a conveyor 702 having a roll 704, a belt 706 and a second roll 708, for transporting the particulate waste 12 into and out of a radio frequency treatment chamber 710, to which are connected a waveguide below cutoff 712 at the inlet end and a waveguide below cutoff 714 at the outlet end. The radio frequency treatment chamber 710 includes a top wall 716, a bottom wall 718, an end wall 720 and an end wall 722, as well as a pair of side walls. Optionally, a nitrogen system or steam sweep system may be connected to the radio frequency treatment chamber 710, although none is shown. A plurality of flat exciter electrodes 730 or other antenna-like applicators, each being driven by a source of radio frequency energy 732, are coupled through a matching network 734 to the plate 730. A control 736 is connected to the source of radio frequency energy and via a cable 738 to a sensing electrode 740 for monitoring an interior region 750 of the radio frequency treatment chamber 710 defined by the walls of the chamber. A hopper 760 contains the material or waste 12 which is fed by a duct 762 to the conveyor 702. The waste is carried through the inlet waveguide below cutoff 712 to the treatment region 750 where vapors are driven off and collected by a duct 770 which feeds an effluent treatment system 772 of the type previously disclosed. Purified gases, such as air and carbon dioxide, as well as possibly water vapor, are released to the environment through a duct 774. Dried residue 780 exits the exit tunnel 714 and is deposited in a waste container 782 for storage or further processing.

The multiplicity of parallel plate exciters, as shown in FIG. 16, is used to tailor the heating rate to the conductivity condition of the material being treated. For example, a different frequency and field intensity would be needed to heat the incoming moist material. As the material dries, a different field intensity and possibly a different frequency might also be employed. Finally, as the material is completely dried out, the absorption is also reduced; however, the need to supply energy to evaporate the water is also reduced. As a consequence, the two requirements tend to offset each other but it is expected that either a higher frequency or higher field intensities usually, not always, be required in the latter portions of the heating process. However, owing to the widely varying characteristics of the different materials, it is not possible to determine the precise field intensity and frequency requirements. The arrangement shown in FIG. 16 allows complete flexibility in this regard since each of the applicator units is controlled by temperature sensors along the flow path of the material. In additionl to the parallel plate applicators, other types of antenna applicators may also be employed. Control of field intensities via the power supplied to each of the applicators can be controlled along with enhancing the height of the parallel plate applicators as well.

Figure 17A:
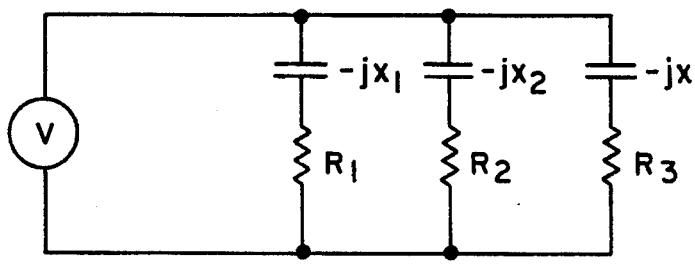
FIGS. 17A, 17B and 17C are schematic representations of the electrical characteristics of various types of radio frequency treatment units embodying the present invention.
Figure 17B:
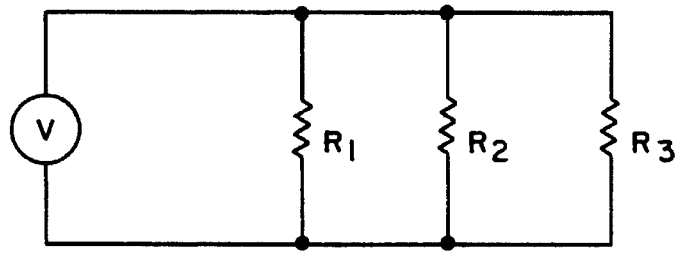

FIG. 17 illustrates the benefits of controlling the air gap to mitigate possible thermal runaway problems. In FIG. 17A, material under a parallel plate applicator, for example, is envisioned. In each portion of the material, displacement currents are introduced via an air gap simulated as a partial capacitor. These are represented by reactances of X1, X2 and X3. Once displacement currents are introduced to the material, the absorption effects are represented by R1, R2 and R3 for each component of the displacement current. If the parallel plate is very close to the top of the material, the capacitive reactance is very small and can be neglected as illustrated in FIG. 17B. In this instance, a constant voltage can be assumed to be applied to various portions of the material as illustrated. In this case, the heating rate is proportional to $V^2/R$ or $V^2r$. As noted in FIG. 2, the conductivity typically can radically increase above a specified temperature typically above about 300° C. In this case, as the conductivity increases, the local heating effect also increases and thereby reinforces itself to cause the material to go to a higher temperature and higher conductivity thereby causing a thermal runaway effect.

Figure 17C:
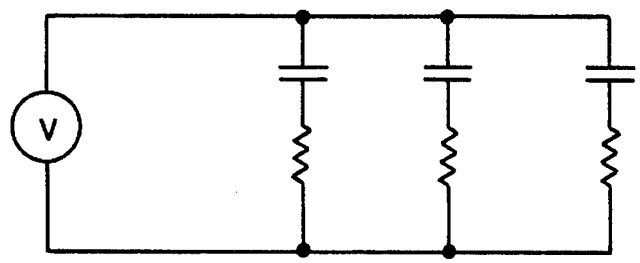

On the other hand, as illustrated in FIG. 17C, if the material is significantly separated from the exciter electrode by a predetermined value, then the reactive component of the partial capacitance is large compared with the existing developments. Under these circumstances, the individual currents will be determined by the partial capacitance and the currents will be equal to the applied voltage as shown in this equivalent circuit divided by each of the capacitive reactances. In this case, the power is governed by a constant current system which, if the conductivity increases, causes the dissipated power to decrease rather than increase as the conductivity increases. By so doing, the deleterious effects of thermal runaway are largely mitigated.

FIG. 18 shows the sweep gas injection and preheating system 876 and effluent treatment system 204 that can be used with certain embodiments of the current inventions such as the ones described in FIGS. 8 and 9. The radio frequency heating chamber 850 consists of a perforated conveyor belt 858 to carry waste containers 852 containing the hazardous waste 854. The bottom wall 856 of the waste container 852 is perforated to facilitate the withdrawal of vapors and gases from the hazardous waste 854 using the blower 866. A temperature sensor 868 is used to measure the temperature of the hazardous waste 854 while it is being processed inside the radio frequency heating chamber 850. A cable 870 transmits the temperature signal to a control station 872. When the hazardous waste reaches a predetermined temperature, the control station 872 activates the sweep gas injection and preheating system 876, and the sweep gases are supplied to the hazardous waste 854 using a pipe 878. A vapor collection line 880 is placed under the conveyor 858 with perforations 862 corresponding to the location of waste container 852 and the vapor withdrawal system 862. Vacuum applied by the blower 866 will provide a reasonable seal between the bottom 856 of the waste container 852, the conveyor 858, and the vapor collection line 862. Such a system will ensure that substantially all of the sweep gas introduced through pipe 878 will flow through the hazardous waste 854. The sweep gases, vapors and non-condensable gases generated from processing of hazardous waste 854, are conveyed to the treatment system 204 using a blower 866. This illustrates the use of the sweep gas injection and preheating system 876 and effluent treatment system 204 for semi-continuous processing of hazardous waste 854. It is within the scope of the present invention to use the system generally described in FIG. 18 for continuous processing of hazardous waste using specific embodiments such as the ones described in FIGS. 8, 9 and 16. For example, the speed of movement of the conveyor 858 can be adjusted such that the waste is preheated to the desired temperature before it travels to the vapor collection line 880. This will permit continuous injection of the sweep gases and continuous removal of the vapors and non-condensable gases.

What is claimed is:

1. Apparatus for treating bulk hazardous waste, comprising:

a radio frequency waste treatment chamber having a wall with an interior surface defining an atmospheric pressure waste treatment region;

means for energizing said atmospheric pressure waste treatment region with radio frequency energy having a frequency of about 500 kilohertz to about 100 megahertz which propagates through the waste treatment region, the bulk hazardous waste being heated by the radio frequency energy, without ionizing gases within the waste treatment region, in order to evolve a hazardous vapor and to leave a residue;

means for maintaining the interior surface of the wall at least substantially as hot as the waste being treated to prevent the evolved hazardous vapor from condensing on said interior surface of said wall and recontaminating the residue; and a hazardous vapor collector for collecting and storing the evolved hazardous vapor.

2. Apparatus according to claim 1, wherein said means for maintaining comprises a guard heater positioned outside said waste treatment region in proximity to said wall.

3. Apparatus according to claim 1, wherein said means for maintaining means comprises an insulator.

4. Apparatus for treating bulk hazardous waste, comprising:

a radio frequency waste treatment chamber having a wall with an interior surface defining an atmospheric pressure waste treatment region;

means for continuously passing bulk hazardous waste through the atmospheric pressure waste treatment region;

means for energizing said atmospheric pressure waste treatment region with radio frequency energy having a frequency of about 500 kilohertz to about 100 megahertz which propagates through the waste treatment region, the bulk hazardous waste being heated by the radio frequency energy, without ionizing gases within the waste treatment region, in order to evolve a hazardous vapor and to leave a residue;

means for maintaining the interior surface of the wall at least substantially as hot as the waste being treated to prevent the evolved hazardous vapor from condensing on said interior surface of said wall and recontaminating the residue; and a hazardous vapor collector for collecting and storing the evolved hazardous vapor.

5. Apparatus according to claim 1, wherein said means for maintaining comprises a guard heater positioned outside said waste treatment region in proximity to said wall.

6. Apparatus according to claim 1, wherein said means for maintaining comprises an insulator.

7. Apparatus for treating bulk hazardous waste, comprising:

a radio frequency waste treatment chamber having a wall with an interior surface defining an atmospheric pressure waste treatment region;

means for passing bulk hazardous waste through said atmospheric pressure waste treatment region;

means for energizing said atmospheric pressure waste treatment region with radio frequency energy having a frequency of about 500 kilohertz to about 100 megahertz which propagates through the waste treatment region, the bulk hazardous waste being heated by the radio frequency energy, without ionizing gases within the waste treatment region, in order to evolve a vapor and to leave a residue;

means for maintaining the interior surface of the wall at least substantially as hot as the waste being treated to prevent the evolved hazardous vapor from condensing on said interior surface of said wall and recontaminatinq the residue; and a hazardous vapor collector for collecting and storing the evolved hazardous vapor.

8. Apparatus according to claim 1, wherein said means for maintaining comprises a guard heater positioned outside said waste treatment region in proximity to said wall.

9. Apparatus according to claim 1, wherein said means for maintaining comprises an insulator.

10. A method for treating bulk hazardous waste comprising the steps of:

disposing bulk hazardous waste in an atmospheric pressure waste treatment region defined by the interior surface of a wall of a waste treatment chamber;

propagating radio frequency energy having a frequency in the range of about 500 kilohertz to about 100 megahertz through said radio frequency waste region, without ionizing gases within the waste treatment region, in order to heat the bulk hazardous waste by the radio frequency energy to evolve a hazardous vapor and to leave a residue;

maintaining the interior surface of the wall at least substantially as hot as the waste being treated to prevent the evolved hazardous vapor from condensing on said interior surface of said wall and recontaminatinq the residue;

collecting the hazardous vapor; and storing the hazardous vapor.

* * * * *